(12) United States Patent
Cannas et al.

(10) Patent No.: US 11,097,259 B2
(45) Date of Patent: Aug. 24, 2021

(54) CATALYST FOR CURABLE COMPOSITIONS CONTAINING HEXAHYDROTRIAZINE STRUCTURAL UNITS

(71) Applicant: SIKA TECHNOLOGY AG, Baar (CH)

(72) Inventors: Rita Cannas, Dübendorf (CH); Urs Burckhardt, Zürich (CH)

(73) Assignee: SIKA TECHNOLOGY AG, Baar (CH)

( * ) Notice: Subject to any disclaimer, the term of this patent is extended or adjusted under 35 U.S.C. 154(b) by 283 days.

(21) Appl. No.: 16/318,661

(22) PCT Filed: Jul. 17, 2017

(86) PCT No.: PCT/EP2017/068032
§ 371 (c)(1),
(2) Date: Jan. 17, 2019

(87) PCT Pub. No.: WO2018/015344
PCT Pub. Date: Jan. 25, 2018

(65) Prior Publication Data
US 2019/0240649 A1 Aug. 8, 2019

(30) Foreign Application Priority Data
Jul. 18, 2016 (EP) ................................. 16179945

(51) Int. Cl.
| | | |
|---|---|---|
| *C07D 251/04* | (2006.01) | |
| *B01J 31/02* | (2006.01) | |
| *C07D 403/06* | (2006.01) | |
| *C07D 403/14* | (2006.01) | |
| *C07F 7/08* | (2006.01) | |
| *C07F 7/18* | (2006.01) | |
| *C08G 18/48* | (2006.01) | |
| *C08G 18/75* | (2006.01) | |
| *C08G 18/82* | (2006.01) | |
| *C08J 3/24* | (2006.01) | |
| *C09D 175/08* | (2006.01) | |
| *C09J 175/08* | (2006.01) | |
| *C09K 3/10* | (2006.01) | |

(52) U.S. Cl.
CPC ....... *B01J 31/0275* (2013.01); *B01J 31/0244* (2013.01); *B01J 31/0271* (2013.01); *C07D 251/04* (2013.01); *C07D 403/06* (2013.01); *C07D 403/14* (2013.01); *C07F 7/0838* (2013.01); *C07F 7/1804* (2013.01); *C08G 18/4825* (2013.01); *C08G 18/755* (2013.01); *C08G 18/82* (2013.01); *C08J 3/24* (2013.01); *C09D 175/08* (2013.01); *C09J 175/08* (2013.01); *C09K 3/1021* (2013.01); *B01J 2231/005* (2013.01); *C09K 2200/0685* (2013.01)

(58) Field of Classification Search
CPC .. C07D 253/00; C07D 403/06; C07D 403/14; C07D 251/04; B01J 31/0275; B01J 31/0244; C07F 7/0838
See application file for complete search history.

(56) References Cited

U.S. PATENT DOCUMENTS 4,291,151 A 9/1981 Mark

FOREIGN PATENT DOCUMENTS

| | | |
|---|---|---|
| DE | 1 769 043 A1 | 9/1971 |
| DE | 31 40 635 A1 | 4/1983 |
| EP | D 007 440 A1 | 2/1980 |
| EP | D 872 505 A1 | 10/1998 |
| EP | 2 268 743 A2 | 1/2011 |
| FR | 2123576 * | 12/1970 |
| GB | 1 257 385 A | 12/1971 |
| JP | 2011-528722 A | 11/2011 |
| WO | 2009/118307 A2 | 10/2009 |
| WO | 2010/043353 A1 | 4/2010 |
| WO | 2015/024813 A1 | 2/2015 |
| WO | 2015/158859 A2 | 10/2015 |
| WO | 2015/158860 A1 | 10/2015 |
| WO | 2015/158863 A1 | 10/2015 |
| WO | 2015/158864 A1 | 10/2015 |
| WO | 2015/193208 A2 | 12/2015 |

OTHER PUBLICATIONS

Kawasaki C., Bitamin vol. 25, issue 5, p. 402-405 (Year: 1962).*
Sep. 25, 2017 International Search Report issued in International Patent Application No. PCT/EP2017/068032.
Jan. 22, 2019 International Preliminary Report on Patentability issued in International Patent Application No. PCT/EP2017/068032.

* cited by examiner

*Primary Examiner* — Mark S Kaucher
(74) *Attorney, Agent, or Firm* — Oliff PLC

(57) ABSTRACT

A compound containing at least one hexahydrotriazine unit of formula (I) having at least one amidine or guanidine group and to the use thereof as a catalyst for the crosslinking of a functional compound, in particular a polymer including silane groups. The compound contains at least one hexahydrotriazine unit of formula (I) is producible in a simple process from readily available feedstocks, odorless at room temperature, non-volatile and largely non-toxic. The compound accelerates the crosslinking of functional polymers surprisingly well and by simple variation of the substituents is variable such that it has very good compatibility in different polymers as a result of which such compositions do not have a propensity for migration-based defects such as separation, exudation or substrate contamination.

15 Claims, No Drawings

CATALYST FOR CURABLE COMPOSITIONS CONTAINING HEXAHYDROTRIAZINE STRUCTURAL UNITS

TECHNICAL FIELD

The invention relates to hexahydrotriazines having amidine or guanidine groups and to the use thereof as catalyst for curable compositions, especially based on polymers having silane groups.

PRIOR ART

Curable compositions play a significant role in many industrial applications, for example as adhesives, sealants or coatings. The curing thereof is brought about by crosslinking reactions which proceed via reactive groups, for example silane groups, isocyanate groups, epoxy groups, hydroxyl groups or amino groups, wherein these react with themselves or one another following a mixing operation or through heating or through contact with moisture, and hence bind the formation components present in the composition covalently to form a polymeric network. Acceleration of such crosslinking reactions is frequently accomplished using catalysts. These are very often substances of toxicological concern which constitute a potential hazard to users and the environment, especially after the curing of the composition, if the catalyst or degradation products thereof are released by outgassing, migration or washing-out. Compositions curable at room temperature that are based on polymers having silane groups are confronted with this problem to a significant degree. Polymers having silane groups here are especially polyorganosiloxanes, which are commonly referred to as "silicones" or "silicone rubbers", and organic polymers having silane groups, which are also referred to as "silane-functional polymers", "silane-modified polymers" (SMP) or "silane-terminated polymers" (STP). The crosslinking thereof proceeds via the condensation of silanol groups to form siloxane bonds and is conventionally catalyzed by means of organotin compounds such as dialkyltin(IV) carboxylates in particular. These are notable for very high activity in relation to the silanol condensation and are very hydrolysis-resistant, but they are harmful to health and a severe water pollution hazard. They are often combined with further catalysts, mainly basic compounds, such as amines in particular, which particularly accelerate the preceding hydrolysis of the silane groups.

Because greater weight is being given to EHS aspects by professional organizations and users and because of stricter government regulation, there have been increased efforts for some time to replace organotin compounds with other catalysts of lower toxicity. For instance, organotitanates, -zirconates and -aluminates have been described as alternative metal catalysts. However, these usually have lower catalytic activity in relation to the silanol condensation and bring about much slower crosslinking. Because of their lack of hydrolysis stability, they can lose a large part of their activity in the course of storage of the composition as a result of residual moisture in the ingredients, which causes the curing to slow significantly or stop entirely.

A further known alternative to organotin compounds is highly basic nitrogen compounds from the class of the amidines and guanidines, which can be used in combination with the metal catalysts mentioned or else alone. However, many of the commonly used amidine and guanidine catalysts, such as, in particular, 1,8-diazabicyclo[5.4.0]undec-7-ene (DBU) and 1,1,3,3-tetramethylguanidine (TMG), are volatile and odorous substances that are likewise harmful to health and hazardous to the environment. Moreover, they have a tendency to migrate because of low compatibility in the composition and hence to cause separation, exudation or substrate soiling.

Further amidine and/or guanidine catalysts are known from WO 2009/118307, WO 2010/043353, WO 2015/158859, WO 2015/158860, WO 2015/158863 and WO 2015/193208. However, these catalysts are still capable of improvement with regard to their catalytic activity and/or compatibility in different polymer systems and the variability of their properties.

DE 1 769 043 discloses hexahydrotriazine catalysts for the production of polyurethane foams.

EP 0 872 505 discloses hexahydrotriazine catalysts for epoxy resin compositions.

But these known hexahydrotriazine catalysts have comparatively low activity, especially for the crosslinking of silane groups.

SUMMARY OF THE INVENTION

It is therefore an object of the present invention to provide a catalyst for the crosslinking of curable compositions, especially based on polymers having silane groups, which has high catalytic activity for the crosslinking reaction, low vapor pressure and high compatibility with the composition, and has minimum odor and low toxicity.

This object is achieved by a compound containing at least one hexahydrotriazine unit of the formula (I) as described in claim 1. It contains at least one amidine group or guanidine group and is odorless, nonvolatile and largely nontoxic at room temperature. It shows high catalytic activity for the reaction of many compounds having polymerizable reactive groups, especially for compositions based on polymers having silane groups. The high activity is particularly surprising, given that, on the basis of the relatively high molecular weight and the strong intermolecular interactions via hydrogen bonds, reduced activity would be expected as compared with smaller, less polar and hence more mobile amidines or guanidines.

The compound containing at least one hexahydrotriazine unit of the formula (I) is preparable in a simple process from readily obtainable base materials, and it is possible in a surprisingly simple manner to bond very different structural elements—for example polyalkylene oxide chains, polysiloxane chains, silane groups, guanidine groups and/or amidine groups of identical or different structure—to one another via the hexahydrotriazine ring. It is thus possible in a simple manner to prepare tailored amidine and/or guanidine catalysts that are matched to different functional polymers in terms of compatibility and catalytic activity.

Curable compositions comprising the compound having at least one hexahydrotriazine unit of the formula (I) are not very toxic and have no tendency, either before or after curing, to migration-related defects such as separation, exudation or substrate soiling. They show good storage stability and have pleasant applicability owing to low odor. After the application, they build up strength surprisingly quickly and form mechanically high-quality, stable and low-emission materials.

Further aspects of the invention form the subject matter of further independent claims. Particularly preferred embodiments of the invention form the subject matter of the dependent claims.

WAYS OF EXECUTING THE INVENTION

The invention provides a compound containing at least one hexahydrotriazine unit of the formula (I)

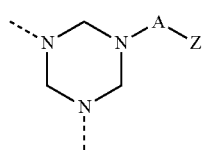

where
A is a divalent hydrocarbyl radical optionally containing heteroatoms, and
Z is an amidine or guanidine group bonded via a nitrogen atom,
where the hexahydrotriazine ring and the Z group are separated from one another by a chain of at least two carbon atoms.

A dotted line in the formulae in this document in each case represents the bond between a substituent and the corresponding molecular radical.

"Primary amino group" and "primary amine nitrogen" refer respectively to an amino group and the nitrogen atom thereof that is bonded to a single organic radical and bears two hydrogen atoms; "secondary amino group" and "secondary amine nitrogen" refer respectively to an amino group and the nitrogen atom thereof that is bonded to two organic radicals which may also together be part of a ring and bears one hydrogen atom; and "tertiary amino group" and "tertiary amine nitrogen" refer respectively to an amino group and the nitrogen atom thereof that is bonded to three organic radicals, two or three of which together may also be part of one or more rings, and does not bear any hydrogen atom.

"Siloxane radical" refers to a radical containing at least one siloxane bond Si—O—Si. "Polysiloxane radical" refers to a siloxane radical containing multiple siloxane bonds in sequence, i.e. Si—(O—Si)$_s$ units with s=2 or more. An (O—Si) unit is referred to here as "siloxane unit".

The term "silane group" refers to a silyl group which is bonded to an organic radical or to a polysiloxane radical and has one to three, especially two or three, hydrolyzable substituents on the silicon atom. Particularly commonly used hydrolyzable substituents are alkoxy radicals. These silane groups are also referred to as "alkoxysilane groups". Silane groups may also be in partly or fully hydrolyzed form.

"Hydroxysilane", "isocyanatosilane", "aminosilane" and "mercaptosilane" refer respectively to organoalkoxysilanes (silanes) having one or more hydroxyl, isocyanato, amino or mercapto groups on the organic radical in addition to the silane group.

The term "organic polymer" encompasses a collective of macromolecules that are chemically homogeneous but differ in relation to degree of polymerization, molar mass and chain length, which has been prepared by a poly reaction (polymerization, polyaddition, polycondensation) and has a majority of carbon atoms in the polymer backbone, and reaction products of such a collective of macromolecules. Polymers having a polyorganosiloxane backbone (commonly referred to as "silicones") are not organic polymers in the context of the present document.

The term "polyether having silane groups" also encompasses organic polymers which have silane groups and, in addition to polyether units, may also contain urethane groups, urea groups or thiourethane groups. Such polyethers having silane groups may also be referred to as "polyurethanes having silane groups". "Molecular weight" is understood in the present document to mean the molar mass (in grams per mole) of a molecule or part of a molecule, also referred to as a "radical". "Average molecular weight" denotes the number-average $M_n$ of an oligomeric or polymeric mixture of molecules or radicals, which is typically determined by means of gel permeation chromatography (GPC) against polystyrene as standard.

"Storage-stable" or "storable" refers to a substance or composition if it can be stored at room temperature in a suitable container over a prolonged period, typically from at least 3 months up to 6 months or more, without any change in its application or use properties, especially in the viscosity and crosslinking rate, to an extent relevant for the use thereof, as a result of the storage.

"Room temperature" refers to a temperature of about 23° C.

The compound containing at least one hexahydrotriazine unit of the formula (I), with regard to its amidine or guanidine groups, may also be in tautomeric form. All possible tautomeric forms are considered to be equivalent. In addition, it may also be in protonated form. It may likewise be in complexed form, especially with cations of zinc, iron or molybdenum.

Preferably, A is a divalent hydrocarbyl radical which has 2 to 50, especially 2 to 20, carbon atoms and optionally contains heteroatoms in the form of ether oxygen or secondary or tertiary amine nitrogen or siloxane units.

More preferably, A is selected from the group consisting of 1,2-ethylene, 1,2-propylene, 1,3-propylene, 1,3-pentylene, 1,5-pentylene, 2-methyl-1,5-pentylene, 1,6-hexylene, 2,2(4),4-trimethyl-1,6-hexamethylene, 1,8-octylene, 1,10-decylene, 1,12-dodecylene, (1,5,5-trimethylcyclohexan-1-yl)methane-1,3, 1,3-cyclohexylenebis(methylene), 1,4-cyclohexylenebis(methylene), 1,3-phenylenebis(methylene), 2- and/or 4-methyl-1,3-cyclohexylene, N-methyl-4-aza-1,7-heptylene, N-ethyl-4-aza-1,7-heptylene, piperazine-1,4-diylbis(1,2-ethylene), piperazine-1,4-diylbis(1,3-propylene), 3-oxa-1,5-pentylene, 3,6-dioxa-1,8-octylene, 4,7-dioxa-1,10-decylene, α,ω-polyoxypropylene having an average molecular weight in the range from about 180 to 500 g/mol and α,ω-(1,3-propylene)polydimethylsiloxane having an average molecular weight in the range from about 350 to 2,000 g/mol.

Most preferably, A is a divalent hydrocarbyl radical which has 2 to 20 carbon atoms and optionally contains heteroatoms in the form of ether oxygen or tertiary amine nitrogen or siloxane units.

More particularly, A is 1,2-ethylene, 1,2-propylene, 1,3-propylene, 2-methyl-1,5-pentylene, 1,6-hexylene, 2,2(4),4-trimethyl-1,6-hexamethylene, 1,8-octylene, 1,10-decylene, 1,12-dodecylene, (1,5,5-trimethylcyclohexan-1-yl)methane-1,3, 1,3-cyclohexylenebis(methylene), 1,4-cyclohexylenebis(methylene), 1,3-phenylenebis(methylene) or 2- and/or 4-methyl-1,3-cyclohexylene. Such a compound containing at least one hexahydrotriazine unit of the formula (I) has particularly good obtainability and is particularly active as catalyst.

In addition, A is especially preferably α,ω-polyoxypropylene having an average molecular weight in the range from about 180 to 500 g/mol. Such a compound containing at least one hexahydrotriazine unit of the formula (I) has particularly good compatibility in curable compositions based on polyether polymers, especially polyethers having silane groups.

In addition, A is especially preferably α,ω-(1,3-propylene)polydimethylsiloxane having an average molecular weight in the range from about 350 to 2,000 g/mol. Such a compound containing at least one hexahydrotriazine unit of the formula (I) has particularly good compatibility in curable compositions based on polyorganosiloxane polymers.

Z is preferably

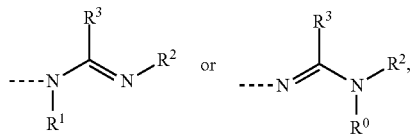

where
R⁰ is a hydrogen radical or an alkyl or cycloalkyl or aralkyl radical having 1 to 8 carbon atoms, R¹ is a hydrogen radical or an alkyl or cycloalkyl or aralkyl radical having 1 to 8 carbon atoms or together with R² is R⁶, R² is a hydrogen radical or an alkyl, cycloalkyl or aralkyl radical which has 1 to 18 carbon atoms and optionally contains ether oxygen or tertiary amine nitrogen, or together with R¹ is R⁶, R³ is —NR⁴R⁵ or a hydrogen radical or an alkyl or cycloalkyl or aralkyl radical having 1 to 12 carbon atoms, where
  R⁴ and R⁵ are each independently a hydrogen radical or an alkyl, cycloalkyl or aralkyl radical which has 1 to 18 carbon atoms and optionally contains ether oxygen or tertiary amine nitrogen,
  R⁶ is an optionally substituted 1,2-ethylene, 1,3-propylene or 1,4-butylene radical having 2 to 12 carbon atoms,
  R² and R⁰ together may also be an alkylene radical which has 3 to 6 carbon atoms and optionally contains ether oxygen or tertiary amine nitrogen,
  R² and R³ together may also be an alkylene radical having 3 to 6 carbon atoms,
  R⁴ and R⁵ together may also be an alkylene radical which has 4 to 7 carbon atoms and optionally contains ether oxygen or tertiary amine nitrogen, and
  R² and R⁵ together may also be an alkylene radical having 2 to 12 carbon atoms.

R¹ is preferably a hydrogen radical or an alkyl radical having 1 to 4 carbon atoms, or together with R² is R⁶.

R² is preferably an alkyl, cycloalkyl or aralkyl radical which has 1 to 12 carbon atoms, especially 1 to 8 carbon atoms, and optionally contains an ether oxygen or tertiary amine nitrogen, or together with R¹ is R⁶.

In one embodiment, Z is an amidine group. In this case, R³ is a hydrogen radical or an alkyl or cycloalkyl or aralkyl radical having 1 to 12 carbon atoms. A compound having amidine groups and containing at least one hexahydrotriazine unit has the advantage that it is less sensitive to hydrolysis by moisture present, and when used as a catalyst it does not have quite as high a catalytic activity and can therefore be used in a somewhat higher amount and hence is less prone to disturbance resulting from other constituents of a composition, especially the impurities present therein.

R³ here is preferably a hydrogen radical or an alkyl radical having 1 to 4 carbon atoms, more preferably a hydrogen radical or methyl radical.

R¹ here is preferably an alkyl radical having 1 to 4 carbon atoms or together with R² is R⁶. More preferably, R¹ and R² together are R⁶.

More preferably, Z is thus an amidine group in which R³ is a hydrogen radical or an alkyl radical having 1 to 4 carbon atoms, especially a hydrogen radical or methyl radical, and R¹ and R² together are R⁶.

Thus, Z more preferably represents an amidine group of the formula

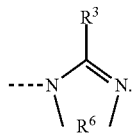

Such an amidine group is obtainable in a particularly simple manner and shows high catalytic activity.

R⁶ preferably has 2 to 6 carbon atoms.

R⁶ is preferably 1,2-ethylene, 1,2-propylene, 1,3-propylene, 2-methyl-1,2-propylene, 2,2-dimethyl-1,3-propylene, 1,3-butylene, 1,4-butylene, 1,3-pentylene, 1,2-cyclohexylene, 1,3-cyclohexylene or 2(4)-methyl-1,3-cyclohexylene, especially 1,2-ethylene, 1,2-propylene, 1,3-propylene, 2-methyl-1,2-propylene, 2,2-dimethyl-1,3-propylene, 1,3-butylene or 1,3-pentylene, more preferably 1,2-ethylene or 1,3-propylene, most preferably 1,3-propylene.

Most preferably, R³ is methyl and R¹ and R² together are 1,3-propylene. Such an amidine group has particularly high catalytic activity and is preparable in a particularly simple manner.

In a further embodiment, Z is an aliphatic guanidine group. In this case, R³ is —NR⁴R⁵.

A compound having guanidine groups and containing at least one hexahydrotriazine unit has the advantage that, when used as catalyst for the crosslinking of silane groups, it has very particularly high catalytic activity.

R¹ and R⁰ here are preferably each a hydrogen radical.

R⁴ is preferably a hydrogen radical.

R⁵ is preferably an alkyl, cycloalkyl or aralkyl radical which has 1 to 12 carbon atoms, especially 1 to 8 carbon atoms, and optionally contains an ether oxygen or tertiary amine nitrogen.

More preferably, Z is thus a guanidine group in which R³ is —NR⁴R⁵, R¹, R⁰ and R⁴ are each a hydrogen radical, and R² and R⁵ are each independently an alkyl, cycloalkyl or aralkyl radical which has 1 to 12 carbon atoms and optionally contains an ether oxygen or tertiary amine nitrogen.

Thus, Z more preferably represents a guanidine group of the formula

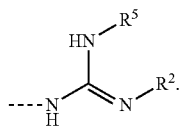

Such a guanidine group is obtainable in a particularly simple manner and in high purity.

R² and R⁵ here are preferably each independently ethyl, isopropyl, tert-butyl, 3-(dimethylamino)propyl or cyclohexyl, especially isopropyl or cyclohexyl.

The compound containing at least one hexahydrotriazine unit of the formula (I) is preferably selected from compounds of the formula (II) and compounds of the formula (III)

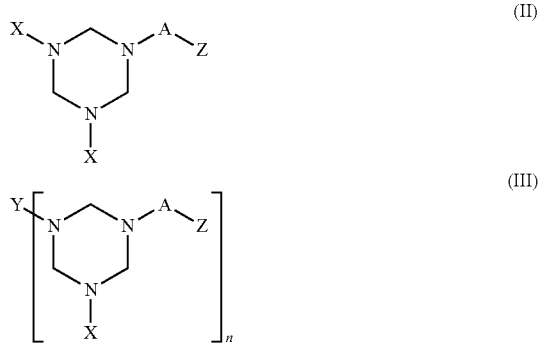

where

X is -A-Z or a monovalent hydrocarbyl radical which has 1 to 30 carbon atoms and optionally contains heteroatoms, Y is an n-valent hydrocarbyl radical which has 2 to 30 carbon atoms and optionally contains heteroatoms, and n is 2 or 3, where, in the case of compounds of the formula (III), the hexahydrotriazine rings are each separated from one another by a chain of at least two carbon atoms.

Preferably, X is -A-Z or an alkyl or cycloalkyl or aralkyl radical which has 1 to 20 carbon atoms and optionally has ether groups, hydroxyl groups, amino groups, silane groups or siloxane units.

In a preferred embodiment, the compound of the formula (II) or (III) contains at least one X radical which is an alkyl or cycloalkyl or aralkyl radical having at least one tertiary amino group and having 1 to 20 carbon atoms, especially 3-(dimethylamino)propyl. Such a compound is particularly suitable as catalyst for curable polyurethane compositions.

More preferably, X is a radical selected from -A-Z, methyl, ethyl, propyl, isopropyl, butyl, isobutyl, sec-butyl, tert-butyl, hexyl, octyl, 2-ethylhexyl, cyclohexyl, benzyl, 3-(dimethylamino)propyl, methoxyethyl, methoxyethoxyethyl, trimethoxysilylpropyl, triethoxysilylpropyl and ω-alkoxypoly(dimethylsiloxane)prop-3-yl having an average molecular weight in the range from about 350 to 2,000 g/mol, where alkoxy is especially methoxy, ethoxy, propoxy, isopropoxy, butoxy, isobutoxy, tert-butoxy or the isomeric pentoxy or hexyloxy radicals.

Preferably, n is 2.

Preferably, Y is an alkylene radical which has 2 to 20 carbon atoms and optionally contains heteroatoms in the form of ether oxygen, amine nitrogen or siloxane units.

More preferably, Y is selected from the group consisting of 2-methyl-1,5-pentylene, 1,6-hexylene, 2,2(4),4-trimethyl-1,6-hexamethylene, 1,8-octylene, 1,10-decylene, 1,12-dodecylene, (1,5,5-trimethylcyclohexan-1-yl)methane-1,3, 1,3-cyclohexylenebis(methylene), 1,4-cyclohexylenebis(methylene), 1,3-phenylenebis(methylene), 2- and/or 4-methyl-1,3-cyclohexylene, N-methyl-4-aza-1,7-heptylene, N-ethyl-4-aza-1,7-heptylene, piperazine-1,4-diylbis(1,2-ethylene), piperazine-1,4-diylbis(1,3-propylene), 3-oxa-1,5-pentylene, 3,6-dioxa-1,8-octylene, 4,7-dioxa-1,10-decylene, α,ω-polyoxypropylene having an average molecular weight in the range from about 180 to 500 g/mol and α,ω-(1,3-propylene)polydimethylsiloxane having an average molecular weight in the range from about 350 to 2,000 g/mol.

Among these, preference is given to α,ω-polyoxypropylene having an average molecular weight in the range from about 180 to 500 g/mol. These compounds of the formula (III) are particularly suitable as catalyst for functional polyether polymers.

Among these, in addition, preference is given to α,ω-(1,3-propylene)polydimethylsiloxane having an average molecular weight in the range from about 350 to 2,000 g/mol. These compounds of the formula (III) are particularly suitable as catalyst for functional polyorganosiloxane polymers.

Preference is given to compounds of the formula (II) having an average of one or two guanidine groups. Compounds of this kind are typically liquid at room temperature and thus easy to handle, and when used as catalyst they enable curable compositions having good storage stability and rapid crosslinking.

Preference is further given to compounds of the formula (II) having an average of one guanidine group and one or two amidine groups. Compounds of this kind are typically liquid at room temperature and thus easy to handle, and when used as catalyst they enable curable compositions having good storage stability and rapid crosslinking.

Preference is further given to compounds of the formula (II) or of the formula (III) that have an average of two or three or four amidine groups. Compounds of this kind are often liquid at room temperature and thus easy to handle, and when used as catalyst they enable curable compositions having good storage stability and rapid crosslinking.

Compounds of the formula (II) or (III) that contain siloxane units are of particularly good compatibility with polyorganosiloxane polymers and hence particularly suitable as catalyst for such systems.

Compounds of the formula (II) or (III) that contain polyoxyalkylene units are of particularly good compatibility with polyether polymers and hence particularly suitable as catalyst for such systems.

Compounds of the formula (II) or (III) that contain further tertiary amino groups as well as the hexahydrotriazine ring are particularly active as catalyst for compositions having isocyanate groups.

The invention further provides a process for preparing the compound containing at least one hexahydrotriazine unit of the formula (I) by reacting at least one amine of the formula $H_2N$-A-Z and optionally at least one further primary amine with formaldehyde or a formaldehyde-releasing compound, especially paraformaldehyde or 1,3,5-trioxane, with removal of water.

The process is performable in a surprisingly rapid and simple manner, especially without the use of auxiliaries and without requiring complex purification of the reaction product, and proceeds from commercially available, inexpensive starting materials.

The process is preferably conducted at a temperature in the range from 0 to 60° C., especially 20 to 40° C.

The reactants are preferably mixed with one another in any desired sequence, optionally in the presence of an organic solvent, and left to react. The reaction product can be washed with water and then dried, for example over magnesium sulfate. Volatile constituents present are preferably distilled off under reduced pressure.

Such a reaction product can be used without further workup or purification as catalyst for functional polymers or compounds or as catalyst for curable compositions.

Suitable amines of the formula H₂N-A-Z for the process are aminoamidines or aminoguanidines that have a primary amino group.

An aminoamidine of the formula H₂N-A-Z which is preferred for the process has the formula

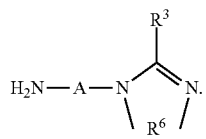

It is especially selected from the group consisting of 1-(2-aminoethyl)-2-methylimidazoline, 1-(3-aminopropyl)-2-methylimidazoline, 1-(2-aminoethyl)-2-methyl-1,4,5,6-tetrahydropyrimidine and 1-(3-aminopropyl)-2-methyl-1,4,5,6-tetrahydropyrimidine.

Among these, preference is given to 1-(2-aminoethyl)-2-methyl-1,4,5,6-tetrahydropyrimidine or 1-(3-aminopropyl)-2-methyl-1,4,5,6-tetrahydropyrimidine. These aminoamidines enable comparatively high catalytic activity.

Such aminoamidines are in turn especially preparable from the reaction of at least one polyalkyleneamine of the formula H₂N-A-NH—R₆—NH₂, such as, in particular, diethylenetriamine, dipropylenetriamine or N-(2-aminoethyl)propane-1,3-diamine (N3 amine), with at least one reagent for introduction of amidine groups, especially an orthoester, a 1,3-keto ester or a nitrile, preferably selected from the group consisting of trimethyl orthoformate, triethyl orthoformate, trimethyl orthoacetate, triethyl orthoacetate, methyl acetoacetate, ethyl acetoacetate, isopropyl acetoacetate, tert-butyl acetoacetate and acetonitrile.

The reaction is preferably conducted at elevated temperature, optionally under elevated pressure and optionally in the presence of a catalyst, wherein elimination products released from the reagent, such as alcohols, esters or amines, are preferably removed during or after the reaction, especially by means of distillation, optionally under reduced pressure.

If trimethyl orthoformate, triethyl orthoformate, trimethyl orthoacetate, triethyl orthoacetate or another orthoester of the formula $R^3$—$C(OR^a)_3$ is used, the reaction is preferably effected at a temperature of 40 to 160° C., especially 60 to 140° C., with removal of the alcohol $R^aOH$ released preferably by distillation. A catalyst is optionally used here, especially an acid.

If methyl acetoacetate, ethyl acetoacetate, isopropyl acetoacetate, tert-butyl acetoacetate or another 1,3-keto ester of the formula $R^3$—$C(O)CH_2C(O)OR^a$ is used, the reaction is preferably effected at a temperature in the range from 20 to 100° C., especially 40 to 80° C., with removal of the ester $CH_3C(O)OR^a$ released preferably by distillation. A catalyst is preferably used here, especially an acid, preferably a sulfonic acid.

If acetonitrile or another nitrile of the formula $R^3$—CN is used, the reaction is preferably effected at a temperature of 60 to 180° C., especially 80 to 160° C., optionally under elevated pressure, with removal of the ammonia released preferably by distillation. A catalyst is preferably used here, especially a Lewis acid, preferably boron trifluoride etherate, lithium perchlorate, zinc chloride, zinc(III) trifluoromethanesulfonate or lanthanum(III) trifluoromethanesulfonate.

An aminoguanidine of the formula H₂N-A-Z which is preferred for the process has the formula

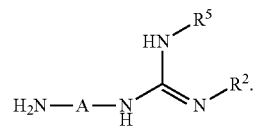

It is especially selected from the group consisting of 1-(2-aminoethyl)-2,3-dicyclohexylguanidine, 1-(2-amino-2(1)-methylethyl)-2,3-dicyclohexylguanidine, 1-(3-aminopropyl)-2,3-dicyclohexylguanidine, 1-(5-amino-4(2)-methylpentyl)-2,3-dicyclohexylguanidine, 1-(6-aminohexyl)-2,3-dicyclohexylguanidine, 1-(6-amino-2,2(4),4-trimethylhexyl)-2,3-dicyclohexylguanidine, 1-(6-amino-3,3(5),5-trimethylhexyl)-2,3-dicyclohexylguanidine, 1-(8-aminooctyl)-2,3-dicyclohexylguanidine, 1-(10-aminodecyl)-2,3-dicyclohexylguanidine, 1-(12-aminododecyl)-2,3-dicyclohexylguanidine, 1-(3-aminomethyl-3,5,5-trimethylcyclohexyl)-2,3-dicyclohexylguanidine, 1-(3-amino-1,5,5-trimethylcyclohexylmethyl)-2,3-dicyclohexylguanidine, 1-(3-aminomethylcyclohexyl)-2,3-dicyclohexylguanidine, 1-(4-aminomethylcyclohexyl)-2,3-dicyclohexylguanidine, 1-(3-aminomethylbenzyl)-2,3-dicyclohexylguanidine, 1-(3-amino-2(4)-methylcyclohexyl)-2,3-dicyclohexylguanidine, 1-(ω-2-aminopropylpolyoxypropylene)-2,3-dicyclohexylguanidine having an average molecular weight in the range from about 400 to 500 g/mol and 1-(ω-3-aminopropyl-α-1,3-propylenepoly(dimethylsiloxane))-2,3-dicyclohexylguanidine having an average molecular weight in the range from about 550 to 2,250 g/mol, and the corresponding compounds with 2,3-diisopropyl groups in place of the 2,3-dicyclohexyl groups.

Such aminoguanidines are in turn especially preparable from the reaction of at least one primary polyamine of the formula H₂N-A-NH₂ with at least one carbodiimide of the formula $R^5$—N=C=N—$R^2$ where $R^2$ and $R^5$ have the definitions described.

The reaction is preferably conducted at elevated temperature, optionally under elevated pressure and optionally in the presence of a catalyst. Preferably, the primary polyamine and the carbodiimide are reacted in a molar ratio of about 1:1.

Particularly suitable carbodiimides are N,N'-diisopropylcarbodiimide (DIC), N,N'-di-tert-butylcarbodiimide, N,N'-dicyclohexylcarbodiimide (DCC) or N-ethyl-N'-(3-dimethylaminopropyl)carbodiimide (EDC), especially N,N'-diisopropylcarbodiimide (DIC) or N,N'-dicyclohexylcarbodiimide (DCC). These reagents are readily available and can be converted efficiently to guanidines.

Particularly suitable primary polyamines of the formula H₂N-A-NH₂ are commercially available amines having two primary amino groups, such as the following in particular:
  aliphatic, cycloaliphatic or arylaliphatic primary
    diamines, especially ethylenediamine, propane-1,2- or -1,3-diamine, 2-methylpropane-1,2-diamine, 2,2-dimethylpropane-1,3-diamine, butane-1,3- or -1,4-diamine, pentane-1,3-diamine (DAMP), pentane-1,5-diamine, 1,5-diamino-2-methylpentane (MPMD), 2-butyl-2-ethylpentane-1,5-diamine (C11 neodiamine), hexane-1,6-diamine, 2,5-dimethylhexane-1,6-diamine, 2,2,4- and 2,4,4-trimethylhexamethylenediamine (TMD), heptane-1,7-diamine, octane-1,8-diamine, nonane-1,9-diamine, decane-1,10-diamine, undecane-1,11-diamine, dodecane-1,12-diamine, 1,2-, 1,3- or 1,4-diaminocyclohexane, bis(4-aminocyclohexyl)methane, bis(4-amino-3-methylcyclohexyl)methane, bis(4-amino-3-ethylcyclohexyl)methane, bis(4-amino-3,5-dimethylcyclohexyl)methane, bis(4-amino-3-ethyl-5-methylcyclohexyl)methane, 1-amino-3-aminomethyl-3,5,5-trimethylcyclohexane (isophoronediamine or IPD), 2- and/or 4-methyl-1,3-diaminocyclohexane, 1,3- or 1,4-bis(aminomethyl)cyclohexane, 2,5(2,6)-bis(aminomethyl)bicyclo[2.2.1]heptane (NBDA), 3(4),8(9)-bis(aminomethyl)tricyclo[5.2.1.0$^{2,6}$]decane, 1,4-diamino-2,2,6-trimethylcyclohexane (TMCDA), 1,8-menthanediamine, 3,9-bis(3-aminopropyl)-2,4,8,10-tetraoxaspiro[5.5]undecane, 1,3-bis(aminomethyl)benzene, 1,4-bis(aminomethyl)benzene, 4-aminomethyloctane-1,8-diamine, N,N'-bis(2-aminoethyl)piperazine, N,N'-bis(3-aminopropyl)piperazine, N,N-bis(3-aminopropyl)methylamine, N,N-bis(3-aminopropyl)ethylamine, N,N-bis(3-aminopropyl)propylamine, N,N-bis(3-aminopropyl)cyclohexylamine, N,N-bis(3-aminopropyl)-2-ethylhexylamine, or products from the double cyanoethylation and subsequent reduction of fatty amines derived from natural fatty acids, such as N,N-bis(3-aminopropyl)dodecylamine or N,N-bis(3-aminopropyl)tallowalkylamine, available as Triameen® Y12D or Triameen® YT (from Akzo Nobel);

aliphatic or cycloaliphatic primary diamines containing ether groups, especially bis(2-aminoethyl) ether, 3,6-dioxaoctane-1,8-diamine, 4,7-dioxadecane-1,10-diamine, 4,7-dioxadecane-2,9-diamine, 4,9-dioxadodecane-1,12-diamine, 5,8-dioxadodecane-3,10-diamine, 4,7,10-trioxatridecane-1,13-diamine, cycloaliphatic diamines containing ether groups from the propoxylation and subsequent amination of 1,4-dimethylolcyclohexane, obtainable especially as Jeffamine® RFD-270 (from Huntsman), polyoxyalkyleneamines having an average molecular weight in the range from 200 to 500 g/mol, as commercially available, for example, under the Jeffamine® trade name (from Huntsman), Polyetheramine (from BASF) and PC Amine® (from Nitroil), characterized in that they bear 2-aminopropyl or 2-aminobutyl end groups, especially Jeffamine® D-230, Jeffamine® D-400, Jeffamine® XTJ-582, Jeffamine® HK-511 or Jeffamine® XTJ-566 (all from Huntsman), or analogous products from BASF and Nitroil;

polyalkyleneamines, especially diethylenetriamine (DETA), triethylenetetramine (TETA), tetraethylenepentamine (TEPA), pentaethylenehexamine (PEHA), polyethylenepolyamine having 5 to 7 ethyleneamine units (called "higher ethylenepolyamine", HEPA), dipropylenetriamine (DPTA), N-(2-aminoethyl)propane-1,3-diamine (N3 amine), N,N'-bis(3-aminopropyl)ethylenediamine (N4 amine), bis(hexamethylentriamine) (BHMT), N3-(3-aminopentyl)pentane-1,3-diamine, N5-(3-aminopropyl)-2-methylpentane-1,5-diamine or N5-(3-amino-1-ethylpropyl)-2-methylpentane-1,5-diamine.

Among these, preference is given to ethylenediamine, propane-1,2-diamine, propane-1,3-diamine, DAMP, pentane-1,5-diamine, MPMD, hexane-1,6-diamine, TMD, octane-1,8-diamine, decane-1,10-diamine, dodecane-1,12-diamine, IPD, 1,3-bis(aminomethyl)cyclohexane, 1,4-bis(aminomethyl)cyclohexane, 1,3-bis(aminomethyl)benzene, 2- and/or 4-methyl-1,3-diaminocyclohexane, N,N-bis(3-aminopropyl)methylamine, N,N-bis(3-aminopropyl)ethylamine, 1,4-bis(aminoethyl)piperazine, 1,4-bis(aminopropyl)piperazine, bis(2-aminoethyl) ether, 3,6-dioxaoctane-1,8-diamine, 4,7-dioxadecane-1,10-diamine, polyoxypropylenediamines having an average molecular weight in the range from about 220 to 500 g/mol or α,ω-bis(3-aminopropyl)polydimethylsiloxanes having an average molecular weight in the range from about 350 to 2,000 g/mol.

For the process for preparing a compound containing at least one hexahydrotriazine unit of the formula (I), as well as at least one amine of the formula H$_2$N-A-Z, at least one further primary amine is optionally used.

The further primary amine is especially an amine having one or two or three primary amino groups and having 1 to 30 carbon atoms and optionally containing heteroatoms.

Suitable amines for this purpose are firstly amines having a primary amino group, such as, in particular, aliphatic, cycloaliphatic or arylaliphatic monoamines optionally having ether groups, especially methylamine, ethylamine, propylamine, isopropylamine, n-butylamine, isobutylamine, sec-butylamine, tert-butylamine, n-pentylamine, isopentylamine, 3-methyl-2-butylamine, n-hexylamine, n-octylamine, 2-ethylhexylamine, n-decylamine, laurylamine, myristylamine, palmitylamine, stearylamine, cyclohexylamine, benzylamine, or fatty amines derived from natural fatty acid mixtures, for example cocoalkylamine, $C_{16}$-$C_{22}$-alkylamine, soyaalkylamine, oleylamine or tallowalkylamine, available, for example, under the Armeen® (from Akzo Nobel) or Rofamin® (from Ecogreen Oleochemicals) brand names, 2-(diethylamino)ethylamine, 2-(diisopropylamino)ethylamine, 3-(dimethylamino)propylamine, 3-(diethylamino)propylamine, 1-diethylamino-4-aminopentane, 2-methoxyethylamine, 2-ethoxyethylamine, 2-butoxyethylamine, 2-cyclohexyloxyethylamine, 2-benzyloxyethylamine, 3-methoxypropylamine, 3-ethoxypropylamine, 3-butoxypropylamine, 3-hexyloxypropylamine, 3-(2-ethylhexyloxy)propylamine, 3-cyclohexyloxypropylamine, 3-phenyloxypropylamine, 2-(2-methoxyethoxy)ethylamine, 3-(2-methoxyethoxy)propylamine, 2(4)-methoxyphenylethylamine, or polyetheramines, especially polyoxyalkyleneamines, especially commercially available products, such as, in particular, Jeffamine® XTJ-581, Jeffamine® M-600, Jeffamine® M-1000, Jeffamine® M-2005, Jeffamine® M-2070 (all from Huntsman), or amines of fatty alcohol or alkylphenol alkoxylates, such as, in particular, Jeffamine® XTJ-247, Jeffamine® XTJ-248, Jeffamine® XTJ-249, Jeffamine® XTJ-435 or Jeffamine® XTJ-436 (all from Huntsman);

aminosilanes, especially 3-aminopropyltrimethoxysilane, 3-aminopropyldimethoxymethylsilane, N-(2-aminoethyl)-3-aminopropyltrimethoxysilane, N-(2-aminoethyl)-3-aminopropylmethyldimethoxysilane, N-(2-aminoethyl)-N'-[3-(trimethoxysilyl)propyl]ethylenediamine, 4-aminobutyltrimethoxysilane, 4-aminobutyldimethoxymethylsilane, 4-amino-3-methylbutyltrimethoxysilane, 4-amino-3-methylbutyldimethoxymethylsilane, 4-amino-3,3-dimethylbutyltrimethoxysilane, 4-amino-3,3- dimethylbutyldimethoxymethylsilane, and the analogs thereof with ethoxy groups in place of the methoxy groups on the silicon;

polyorganosiloxanes having a primary amino group, such as, in particular, α-(3-aminopropyl)-ω-alkoxypoly(dimethylsiloxane) having an average molecular weight in the range from 350 to 2,000 g/mol.

Among these, preference is given to methylamine, ethylamine, propylamine, isopropylamine, n-butylamine, isobutylamine, sec-butylamine, tert-butylamine, n-hexylamine, n-octylamine, 2-ethylhexylamine, cyclohexylamine, benzylamine, 3-(dimethylamino)propylamine, 2-methoxyethylamine, 2-(2-methoxyethoxy)ethylamine, 3-aminopropyltrimethoxysilane, 3-aminopropyltriethoxysilane or α-(3-aminopropyl)-ω-alkoxypoly(dimethylsiloxane) having an average molecular weight in the range from 350 to 2,000 g/mol.

Additionally suitable for this purpose are amines having two or three, especially two, primary amino groups, such as, in particular, the polyamines of the formula $H_2N$-A-$NH_2$ that have already been mentioned. These amines are suitable for the preparation of compounds of the formula (III). Preference is given to MPMD, hexane-1,6-diamine, TMD, octane-1,8-diamine, decane-1,10-diamine, dodecane-1,12-diamine, IPD, 1,3-bis(aminomethyl)cyclohexane, 1,4-bis(aminomethyl)cyclohexane, 1,3-bis(aminomethyl)benzene, 2- and/or 4-methyl-1,3-diaminocyclohexane, N,N-bis(3-aminopropyl)methylamine, N,N-bis(3-aminopropyl)ethylamine, 1,4-bis(2-aminoethyl)piperazine, 1,4-bis(3-aminopropyl)piperazine, bis(2-aminoethyl) ether, 3,6-dioxaoctane-1,8-diamine, 4,7-dioxadecane-1,10-diamine, polyoxypropylenediamines having an average molecular weight in the range from about 220 to 500 g/mol or α,ω-bis(3-aminopropyl)polydimethylsiloxanes having an average molecular weight in the range from about 350 to 2,000 g/mol.

Particular preference is given to MPMD, hexane-1,6-diamine, TMD, octane-1,8-diamine, decane-1,10-diamine, dodecane-1,12-diamine, IPD, 1,3-bis(aminomethyl)cyclohexane, 1,4-bis(aminomethyl)cyclohexane, 1,3-bis(aminomethyl)benzene, 2- and/or 4-methyl-1,3-diaminocyclohexane, polyoxypropylenediamines having an average molecular weight in the range from about 220 to 500 g/mol or α,ω-bis(3-aminopropyl)polydimethylsiloxanes having an average molecular weight in the range from about 350 to 2,000 g/mol.

In a preferred embodiment of the process, an amine of the formula $H_2N$-A-Z is reacted with formaldehyde or a formaldehyde-releasing compound in a molar ratio of about 1:1. This gives rise to compounds of the formula (II) in which X is -A-Z.

It is possible and may be preferable here to use a mixture of different amines of the formula $H_2N$-A-Z, for example a mixture of aminoamidines and aminoguanidines, and/or a mixture in which A represents various radicals, for example a mixture comprising polyoxypropylene radicals and hydrocarbyl radicals without heteroatoms, or a mixture comprising amines with siloxane units and amines without heteroatoms in the A radical.

In a further preferred embodiment of the process, a mixture of amine of the formula $H_2N$-A-Z and an amine having just one primary amino group with formaldehyde or a formaldehyde-releasing compound is converted in such a way that the molar ratio between the primary amino groups and formaldehyde is about 1:1. This gives rise to compounds of the formula (II) in which some of the X radicals are not -A-Z.

In a further preferred embodiment of the process, at least one amine of the formula $H_2N$-A-Z, at least one polyamine having two or three, especially two, primary amino groups and optionally at least one amine having just one primary amino group with formaldehyde or a formaldehyde-releasing compound is converted such that the molar ratio between the primary amino groups and formaldehyde is about 1:1. This gives rise to compounds of the formula (III).

An alternative means of preparing a compound containing at least one hexahydrotriazine unit of the formula (I) involves first reacting an amine of the formula $H_2N$-A-NH—$R_6$—$NH_2$ or $H_2N$-A-$NH_2$ with formaldehyde or a formaldehyde-releasing compound to give a compound having at least one hexahydrotriazine unit of the formula (Ia) or (Ib)

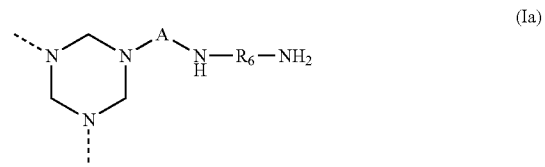

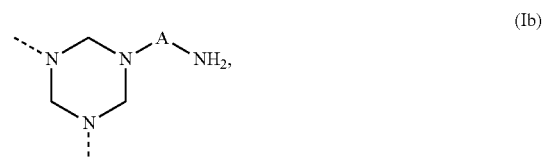

and subsequently reacting this with the reagent for introduction of amidine or guanidine groups to give the desired compound containing at least one hexahydrotriazine unit of the formula (I).

This alternative means of preparation is advantageous especially in the case of amidines in that, for example, a hexahydratriazine compound of the formula (IV) is reacted with a suitable reagent for introduction of amidine groups to give a compound of the formula (IIa).

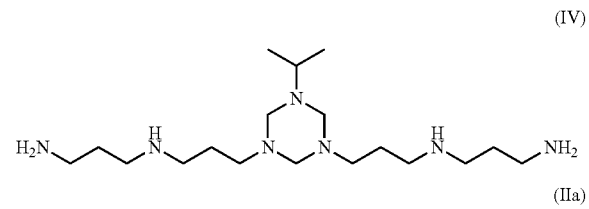

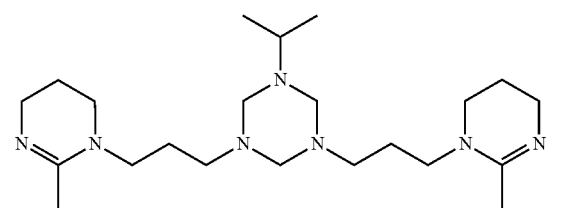

A further alternative means of preparing a compound containing at least one hexahydrotriazine unit of the formula (I) involves reacting at least one hexahydrotriazine of the formula (V) or hexamethylenetriamine of formula (Va)

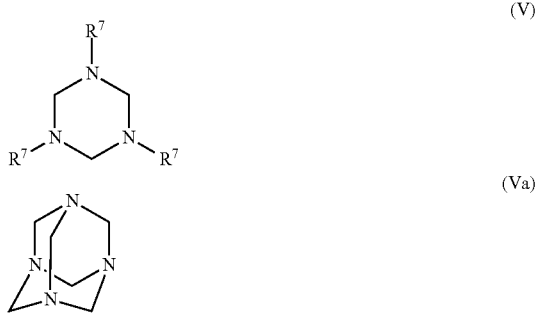

with at least one amine of the formula H$_2$N-A-Z and optionally at least one further primary amine under transamination and release of amine of the formula H$_2$N—R$^7$ or ammonia, where R$^7$ is an alkyl radical having 1 to 6 carbon atoms, especially methyl, ethyl, propyl, isopropyl, butyl, isobutyl or tert-butyl.

The transamination is preferably conducted at elevated temperature, especially at a temperature in the range from 60 to 180° C. Preference is given to constantly removing amine of the formula H$_2$N—R$^7$ or ammonia released by distillation during the transamination.

This preparation can also be conducted in such a way that, for the transamination, rather than the amine of the formula H$_2$N-A-Z, the corresponding amine of the formula H$_2$N-A-NH—R$_6$—NH$_2$ or H$_2$N-A-NH$_2$ is used, and the amidine or guanidine groups are only introduced after the transamination by reaction with a suitable reagent.

The preparation via transamination is advantageous particularly in the case of use of aminosilanes as further amine since the silane groups do not come into contact with water here.

Particularly compounds containing silane groups, for example the compounds of the formula (IIb) or (IIc), are preferably prepared via transamination.

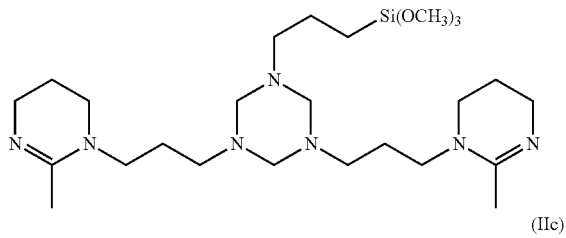

(IIb)

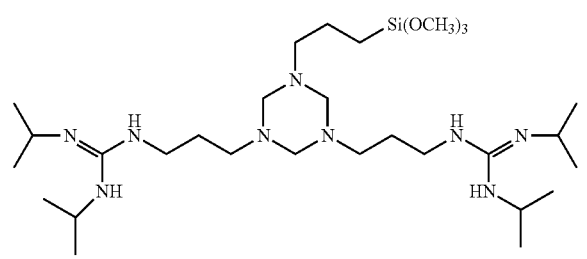

(IIc)

The compound of the formula (IIb), for example, is more preferably prepared by transaminating 1 mol of a hexahydrotriazine of the formula (V) with 2 mol of DPTA and 1 mol of 3-aminopropyltrimethoxysilane and then reacting the product obtained with a suitable reagent for introduction of amidine groups, for example trimethyl orthoacetate.

The compound of the formula (IIc), for example, is more preferably prepared by transaminating 1 mol of a hexahydrotriazine of the formula (V) with 2 mol of 1-(3-aminopropyl)-2,3-diisopropylguanidine and 1 mol of 3-aminopropyltrimethoxysilane.

The invention further provides for the use of the compound containing at least one hexahydrotriazine unit of the formula (I) as catalyst for the crosslinking of a functional compound. This compound containing at least one hexahydrotriazine unit of the formula (I) accelerates the crosslinking or curing of the functional compound or the curing of a composition comprising the functional compound. Via the selection of the substituents in the hexahydrotriazine unit of the compound containing at least one hexahydrotriazine unit of the formula (I), the respective catalytic activity and the compatibility thereof can be optimized to the respective functional compound or to the respective composition comprising the functional compound, such that they have good miscibility and compatibility therewith and do not have a tendency to separation or migration.

The functional compound especially has two or more functional groups that can be cured with moisture or a suitable curing agent to give a polymeric structure. The functional groups are preferably selected from the group consisting of isocyanate groups, silane groups, epoxy groups and cyanate ester groups.

Suitable functional compounds are especially
a polyisocyanate,
a polymer having isocyanate groups, especially a polyurethane polymer having isocyanate groups,
a polymer having silane groups,
a compound having glycidoxy groups, especially a di- or polyfunctional epoxy resin,
a cyanate ester resin, or
a polymer having various functional groups among these, especially a polymer having isocyanate and silane groups or a polymer having isocyanate and epoxy groups.

A preferred functional compound which is crosslinked using the compound containing at least one hexahydrotriazine unit of the formula (I) is a polyisocyanate or a polyurethane polymer having isocyanate groups or a polymer having silane groups.

A suitable polyisocyanate is especially a monomeric diisocyanate, or an oligomer or a polymer or a derivative of a monomeric diisocyanate, or any desired mixture thereof. Oligomers and polymers are understood here to mean homopolymers and -oligomers consisting exclusively of di- or triisocyanate constituents.

Suitable monomeric diisocyanates are especially tolylene 2,4- or 2,6-diisocyanate or any mixtures of these isomers (TDI), diphenylmethane 4,4'-, 2,4'- or 2,2'-diisocyanate or any mixtures of these isomers (MDI), mixtures of MDI and MDI homologs (polymeric MDI or PMDI), phenylene 1,3- or 1,4-diisocyanate, 2,3,5,6-tetramethyl-1,4-diisocyanatobenzene, naphthalene 1,5-diisocyanate (NDI), 3,3'-dimethyl-4,4'-diisocyanatodiphenyl (TODI), dianisidine diisocyanate (DADI), tetramethylene 1,4-diisocyanate, 2-methylpentamethylene 1,5-diisocyanate, hexamethylene 1,6-diisocyanate (HDI), 2,2(4),4-trimethylhexamethylene 1,6-diisocyanate (TMDI), decamethylene 1,10-diisocyanate, dodecamethylene 1,12-diisocyanate, lysine or lysine ester diisocyanate, cyclohexane 1,3- or 1,4-diisocyanate, 1-methyl-2,4- or -2,6-diisocyanatocyclohexane or any desired mixtures of these isomers (HTDI or $H_6$TDI), 1-isocyanato-3,3,5-trimethyl-5-isocyanatomethylcyclohexane (isophorone diisocyanate or IPDI), perhydro(diphenylmethane 2,4'- or 4,4'-diisocyanate) (HMDI or $H_{12}$MDI), 1,4-diisocyanato-2,2,6-trimethylcyclohexane (TMCDI), 1,3- or 1,4-bis(isocyanatomethyl)cyclohexane, m- or p-xylylene diisocyanate (m- or p-XDI), m- or p-tetramethylxylylene 1,3- or 1,4-diisocyanate (m- or p-TMXDI) or bis(1-isocyanato-1-methylethyl)naphthalene. Among these, preference is given to MDI, TDI, IPDI or HDI, especially MDI.

Suitable oligomers, polymers or derivatives of monomeric diisocyanates are especially derived from MDI, TDI, HDI or IPDI.

More preferably, the polyisocyanate is a form of MDI which is liquid at room temperature, especially having a high content of diphenylmethane 4,4'-diisocyanate. What is called "liquid MDI" is either diphenylmethane 4,4'-diisocyanate liquefied by partial chemical modification—especially carbodiimidization or uretonimine formation—or it is a mixture of diphenylmethane 4,4'-diisocyanate with other MDI isomers (2,4'-diphenylmethane diisocyanate and/or 2,2'-diphenylmethane diisocyanate), or with MDI oligomers or MDI homologs, that has been brought about selectively by blending or results from the production process.

A suitable polyurethane polymer having isocyanate groups is especially obtained from the reaction of at least one polyol with a superstoichiometric amount of at least one polyisocyanate, especially a diisocyanate. The reaction is preferably conducted with exclusion of moisture at a temperature in the range from 50 to 160° C., optionally in the presence of suitable catalysts. The excess of polyisocyanate is preferably chosen so as to leave, in the polyurethane polymer after the conversion of all hydroxyl groups, a content of free isocyanate groups in the range from 1% to 30% by weight, preferably 1.5% to 25% by weight, more preferably 2% to 20% by weight. The polyurethane polymer can optionally be prepared with additional use of plasticizers or solvents, in which case the plasticizers or solvents used do not contain any groups reactive toward isocyanates.

Diisocyanates suitable for this purpose are especially MDI, TDI, PMDI, HDI, IPDI, $H_{12}$MDI, or oligomers or derivatives of these diisocyanates.

Polyols suitable for this purpose are especially polyether polyols, preferably polyoxyalkylene polyols, which are polymerization products of ethylene oxide or 1,2-propylene oxide or 1,2- or 2,3-butylene oxide or oxetane or tetrahydrofuran or mixtures thereof, possibly polymerized with the aid of a starter molecule having two or more active hydrogen atoms; polyester polyols, preferably products from the polycondensation of diols or triols with lactones or dicarboxylic acids or esters or anhydrides thereof; polycarbonate polyols; OH-terminal block copolymers having at least two different blocks having polyether, polyester or polycarbonate units; polyacrylate polyols or polymethacrylate polyols; polyhydroxy-functional fats or oils, especially natural fats or oils; or polyhydrocarbon polyols, for example polyhydroxy-functional polyolefins, especially polybutadienepolyols.

Also especially suitable are mixtures of the polyols mentioned.

Especially suitable are diols or triols or mixtures thereof.

The polyurethane polymer having isocyanate groups preferably has an average molecular weight in the range from 350 to 30,000 g/mol, especially 1,000 to 15,000 g/mol.

More preferably, functional compound which is crosslinked using the compound containing at least one hexahydrotriazine unit of the formula (I) is a polymer having silane groups.

The compound containing at least one hexahydrotriazine unit of the formula (I) has a strong catalytic effect on the hydrolysis and condensation reactions of polymers having silane groups. A polymer having silane groups therefore cures rapidly even with a relatively small amount of a compound containing at least one hexahydrotriazine unit of the formula (I) as catalyst and is thus particularly less prone to migration-related defects such as separation or exudation and particularly inexpensive.

The polymer having silane groups is especially selected from the group consisting of polyorganosiloxanes having terminal silane groups and organic polymers having silane groups, as described more specifically hereinafter.

A polyorganosiloxane having terminal silane groups has the advantage that it is particularly water- and light-stable and enables particularly flexible properties. An organic polymer having silane groups has the advantage of having particularly good adhesion properties on a multitude of substrates and being particularly inexpensive.

The invention further provides a curable composition comprising at least one compound containing at least one hexahydrotriazine unit of the formula (I) as catalyst. In this case, this compound accelerates the crosslinking or curing of the composition.

Preferably, the curable composition contains functional groups selected from isocyanate groups, silane groups, epoxy groups and cyanate ester groups.

More preferably, the curable composition contains isocyanate groups and/or silane groups, especially silane groups.

A curable composition containing isocyanate groups is also referred to as curable polyurethane composition.

Preferably, the curable composition comprises at least one polyisocyanate or at least one polyurethane polymer having isocyanate groups or at least one polymer having silane groups, as described above.

Preferably, the curable composition is used for bonding, sealing, insulating, coating or pretreating in building and industrial applications, especially as concrete element adhesive, facade adhesive, parquet adhesive, window profile adhesive, anchoring adhesive, assembly adhesive, bodywork adhesive, pane adhesive, sandwich element adhesive, lining adhesive, laminate adhesive, packaging adhesive, joint sealant, floor grout, spackling compound, sealing membrane, weld or flange seam sealant, cavity seal, building foam, furniture foam, filter foam, insulation foam, sound insulation foam, packaging foam, bodywork foam, floor covering, floor coating, balcony coating, roof coating, concrete protection coating, parking garage coating, pipe coating, anticorrosion coating, textile coating, primer, activator or primer coat, or as molding, semifinished product, film or fiber, especially as cushioning, pillow, mattress, shoe sole, shock absorber, damping element, gasket, tire, roll, bearing, drum, conveyor belt, hose, housing, window profile, insulation panel, model construction panel, sandwich element, fiber composite body, implant, packaging film, lamination film or textile fiber.

In particular, the curable composition is an adhesive or a sealant or a coating.

Preferably, the curable composition comprises at least one polymer having silane groups, especially selected from the group consisting of polyorganosiloxanes having terminal silane groups and organic polymers having silane groups.

A composition of this kind has good storage stability with no propensity to separation, and because of the low toxicity and low volatility of the compound containing at least one hexahydrotriazine unit of the formula (I) allows a low hazard classification and enables low-emissions and low-odor products that cure rapidly and at the same time form a mechanically high-quality and durable material. A particularly advantageous circumstance here is that this material shows barely any propensity to migration-related defects such as exudation or substrate soiling, by contrast with compositions comprising catalysts according to the prior art, for example DBU or TMG. Compositions comprising such catalysts known from the prior art have a propensity to migration effects, which can be manifested prior to curing by separation and after curing by tacky and/or greasy surfaces and/or substrate soiling. Particularly the latter effects are extremely undesirable, since tacky and greasy surfaces are rapidly soiled and are difficult to paint over, and substrate contaminants can lead to lasting discoloration.

In a preferred embodiment, the polymer having silane groups is a polyorganosiloxane having terminal silane groups.

A preferred polyorganosiloxane having terminal silane groups has the formula (VI)

$$(G)_{3-a}-\underset{(R^8)_a}{Si}-O-\left[\underset{R^{10}}{\overset{R^9}{Si}}-O\right]_m-\underset{(R^8)_a}{Si}-(G)_{3-a} \quad (VI)$$

where $R^8$, $R^9$ and $R^{10}$ are each independently a monovalent hydrocarbyl radical having 1 to 12 carbon atoms, G is a hydroxyl radical or an alkoxy, acetoxy, ketoximato, amido or enoxy radical having 1 to 13 carbon atoms, a is 0, 1 or 2, and m is an integer in the range from 50 to about 2,500.

$R^8$ is preferably methyl, vinyl or phenyl.

$R^9$ and $R^{10}$ are preferably each independently an alkyl radical having 1 to 5, preferably 1 to 3, carbon atoms, especially methyl.

G is preferably a hydroxyl radical or an alkoxy or ketoximato radical having 1 to 6 carbon atoms, especially a hydroxyl, methoxy, ethoxy, methylethylketoximato or methylisobutylketoximato radical.

More preferably, G is a hydroxyl radical.

a is preferably 0 or 1, especially 0.

In addition, m is preferably chosen such that the polyorganosiloxane of the formula (VI) has a viscosity at room temperature in the range from 100 to 500,000 mPa·s, especially from 1,000 to 100,000 mPa·s.

Polyorganosiloxanes of the formula (VI) are easy to handle and crosslink with moisture and/or silane crosslinkers to give solid silicone polymers having elastic properties.

Suitable commercially available polyorganosiloxanes of the formula (VI) are available, for example, from Wacker, Momentive Performance Materials, GE Advanced Materials, Dow Corning, Bluestar Silicones or Shin-Etsu.

Preferably, the composition comprises, in addition to the polyorganosiloxane having terminal silane groups, a silane crosslinker, especially a silane of the formula (VII)

$$(R^{11})_q-Si-(G')_{4-q} \quad (VII)$$

where $R^{11}$ is a monovalent hydrocarbyl radical having 1 to 12 carbon atoms,

G' is a hydroxyl radical or is an alkoxy, acetoxy, ketoximato, amido or enoxy radical having 1 to 13 carbon atoms, and q has a value of 0, 1 or 2, especially 0 or 1.

Particularly suitable silanes of the formula (VII) are methyltrimethoxysilane, ethyltrimethoxysilane, propyltrimethoxysilane, vinyltrimethoxysilane, phenyltrimethoxysilane, methyltriethoxysilane, vinyltriethoxysilane, phenyltriethoxysilane, tetramethoxysilane, tetraethoxysilane, methyltris(methylethylketoximo)silane, vinyltris(methylethylketoximo)silane or methyltris(isobutylketoximo)silane.

In a further preferred embodiment, the polymer having silane groups is an organic polymer having silane groups, especially a polyolefin, polyether, polyester, polyamide, poly(meth)acrylate or a mixed form of these polymers, each of which bears one or preferably more than one silane group. The silane groups may be in pendant positions in the chain or in terminal positions and are bonded to the organic polymer via a carbon atom.

More preferably, the organic polymer having silane groups is a polyolefin having silane groups or a polyether having silane groups or a polyester having silane groups or a poly(meth)acrylate having silane groups or a mixed form of these polymers.

Most preferably, the organic polymer having silane groups is a polyether having silane groups.

The silane groups present in the organic polymer having silane groups are preferably alkoxysilane groups, especially alkoxysilane groups of the formula (VIII)

$$----Si-\underset{(R^{13})_x}{|}-(OR^{12})_{3-x} \quad (VIII)$$

where $R^{12}$ is a linear or branched monovalent hydrocarbyl radical having 1 to 5 carbon atoms, especially methyl, ethyl or isopropyl, $R^{13}$ is a linear or branched monovalent hydrocarbyl radical having 1 to 8 carbon atoms, especially methyl, and x has a value of 0 or 1 or 2, preferably 0 or 1, especially 0.

More preferably, $R^{12}$ is methyl or ethyl.

Particular preference is given to trimethoxysilane groups, dimethoxymethylsilane groups or triethoxysilane groups.

Methoxysilane groups have the advantage here that they are particularly reactive and crosslink rapidly, and ethoxysilane groups have the advantage that they are particularly storage-stable and release comparatively nontoxic ethanol in the course of crosslinking.

The organic polymer having silane groups has an average of preferably 1.3 to 4, especially 1.5 to 3, more preferably 1.7 to 2.8, silane groups per molecule. The silane groups are preferably terminal.

The organic polymer having silane groups preferably has an average molecular weight in the range from 1,000 to 30,000 g/mol, especially from 2,000 to 20,000 g/mol.

The organic polymer having silane groups preferably has a silane equivalent weight of 300 to 25,000 g/eq, especially 500 to 15,000 g/eq.

The organic polymer having silane groups may be solid or liquid at room temperature. It is preferably liquid at room temperature.

Most preferably, the organic polymer having silane groups is a polyether having silane groups which is liquid at room temperature, where the silane groups are especially dialkoxysilane groups and/or trialkoxysilane groups, more preferably trimethoxysilane groups or triethoxysilane groups.

Processes for preparing polyethers having silane groups are known to the person skilled in the art.

In a preferred process, polyethers having silane groups are obtainable from the reaction of polyethers containing allyl groups with hydrosilanes, optionally with chain extension using diisocyanates for example.

In a further preferred process, polyethers having silane groups are obtainable from the copolymerization of alkylene oxides and epoxysilanes, optionally with chain extension using diisocyanates for example.

In a further preferred process, polyethers having silane groups are obtainable from the reaction of polyether polyols with isocyanatosilanes, optionally with chain extension using diisocyanates.

In a further preferred process, polyethers having silane groups are obtainable from the reaction of polyethers having isocyanate groups, especially NCO-terminated urethane polyethers from the reaction of polyether polyols with a superstoichiometric amount of polyisocyanates, or with aminosilanes, hydroxysilanes or mercaptosilanes. Polyethers having silane groups from this process are particularly preferred. This process enables the use of a multiplicity of commercially readily available inexpensive starting materials by means of which different polymer properties are obtainable, for example high extensibility, high strength, low modulus of elasticity, low glass transition temperature or high weathering resistance.

It is particularly preferable when the polyether having silane groups is obtainable from the reaction of NCO-terminated urethane polyethers with aminosilanes or hydroxysilanes. Suitable NCO-terminated urethane polyethers are obtainable from the reaction of polyether polyols, especially polyoxyalkylene diols or polyoxyalkylene triols, preferably polyoxypropylene diols or polyoxypropylene triols, with a superstoichiometric amount of polyisocyanates, especially diisocyanates.

It is preferable when the reaction between the polyisocyanate and the polyether polyol is conducted with exclusion of moisture at a temperature of 50° C. to 160° C., optionally in the presence of suitable catalysts, wherein the polyisocyanate has been dosed such that the isocyanate groups thereof are present in a stoichiometric excess in relation to the hydroxyl groups of the polyol. In particular, the excess of polyisocyanate is chosen such that in the resulting urethane polyether, after the reaction of all hydroxyl groups, there remains a content of free isocyanate groups of 0.1% to 5% by weight, preferably 0.2% to 4% by weight, more preferably 0.3% to 3% by weight. Preferred isocyanates are selected from the group consisting of HDI, IPDI, TDI and MDI. Particular preference is given to IPDI or TDI. Most preferred is IPDI. In this way, polyethers having silane groups with particularly good lightfastness are obtained.

Especially suitable as polyether polyols are polyoxyalkylenediols or polyoxyalkylenetriols having a degree of unsaturation lower than 0.02 meq/g, especially lower than 0.01 meq/g, and an average molecular weight in the range from 400 to 25,000 g/mol, especially 1000 to 20,000 g/mol.

In addition to polyether polyols it is also possible to use proportions of other polyols, especially polyacrylate polyols and low molecular weight diols or triols.

Suitable aminosilanes for the reaction with an NCO-terminated urethane polyether are primary and secondary aminosilanes. Preference is given to 3-aminopropyltrimethoxysilane, 3-aminopropyldimethoxymethylsilane, 4-aminobutyltrimethoxysilane, 4-amino-3-methylbutyltrimethoxysilane, 4-amino-3,3-dimethylbutyltrimethoxysilane, N-butyl-3-aminopropyltrimethoxysilane, N-phenyl-3-aminopropyltrimethoxysilane, adducts formed from primary amino-silanes such as 3-aminopropyltrimethoxysilane, 3-aminopropyldimethoxymethylsilane or N-(2-aminoethyl)-3-aminopropyltrimethoxysilane and Michael acceptors such as acrylonitrile, (meth)acrylic esters, (meth)acrylamides, maleic or fumaric diesters, citraconic diesters or itaconic diesters, especially dimethyl or diethyl N-(3-trimethoxysilylpropyl)aminosuccinate. Likewise suitable are analogs of the recited aminosilanes with ethoxy or isopropoxy groups in place of the methoxy groups on the silicon.

Suitable hydroxysilanes for the reaction with an NCO-terminated urethane polyether are especially obtainable from the addition of aminosilanes onto lactones or onto cyclic carbonates or onto lactides.

Aminosilanes suitable for this purpose are especially 3-aminopropyltrimethoxysilane, 3-aminopropyltriethoxysilane, 4-aminobutyltrimethoxysilane, 4-aminobutyltriethoxysilane, 4-amino-3-methylbutyltrimethoxysilane, 4-amino-3-methylbutyltriethoxysilane, 4-amino-3,3-dimethylbutyltrimethoxysilane, 4-amino-3,3-dimethylbutyltriethoxysilane, 2-aminoethyltrimethoxysilane or 2-aminoethyltriethoxysilane. Particular preference is given to 3-aminopropyltrimethoxysilane, 3-aminopropyltriethoxysilane, 4-amino-3,3-dimethylbutyltrimethoxysilane or 4-amino-3,3-dimethylbutyltriethoxysilane.

Suitable lactones are especially γ-valerolactone, γ-octalactone, δ-decalactone or ε-decalactone, especially γ-valerolactone.

Suitable cyclic carbonates are especially 4,5-dimethyl-1,3-dioxolan-2-one, 4,4-dimethyl-1,3-dioxolan-2-one, 4-ethyl-1,3-dioxolan-2-one, 4-methyl-1,3-dioxolan-2-one or 4-(phenoxymethyl)-1,3-dioxolan-2-one.

Suitable lactides are especially 1,4-dioxane-2,5-dione (lactide formed from 2-hydroxyacetic acid, also called "glycolide"), 3,6-dimethyl-1,4-dioxane-2,5-dione (lactide formed from lactic acid, also called "lactide") or 3,6-diphenyl-1,4-dioxane-2,5-dione (lactide formed from mandelic acid).

Preferred hydroxysilanes that are obtained in this way are N-(3-triethoxysilylpropyl)-2-hydroxypropanamide, N-(3-triethoxysilylpropyl)-4-hydroxypentanamide, N-(3-triethoxysilylpropyl)-4-hydroxyoctanamide, N-(3-triethoxysilylpropyl)-5-hydroxydecanamide, N-(3-triethoxysilylpropyl)-2-hydroxypropyl carbamate and the corresponding silanes with methoxy in place of the ethoxy groups.

Suitable hydroxysilanes are additionally also obtainable from the addition of aminosilanes onto epoxides or from the addition of amines onto epoxysilanes. Preferred hydroxysilanes which are obtained in this way are 2-morpholino-4(5)-(2-trimethoxysilylethyl)cyclohexan-1-ol, 2-morpholino-4(5)-(2-triethoxysilyl-ethyl)cyclohexan-1-ol or 1-morpholino-3-(3-(triethoxysilyl)propoxy)propan-2-ol.

Further suitable polyethers having silane groups are commercially available products, especially the following: MS Polymer™ (from Kaneka Corp.; especially the S203H, S303H, S227, S810, MA903 and S943 products); MS Polymer™ or Silyl™ (from Kaneka Corp.; especially the SAT010, SAT030, SAT200, SAX350, SAX400, SAX725, MAX450, MAX951 products); Excestar® (from Asahi Glass Co. Ltd.; especially the S2410, S2420, S3430, S3630 products); SPUR+* (from Momentive Performance Materials; especially the 1010LM, 1015LM, 1050MM products); Vorasil™ (from Dow Chemical Co.; especially the 602 and 604 products); Desmoseal® (from Covestro AG; especially the S XP 2458, S XP 2636, S XP 2749, S XP 2774 and S XP 2821 products), TEGOPAC® (from Evonik Industries AG; especially the Seal 100, Bond 150, Bond 250 products), Polymer ST (from Hanse Chemie AG/Evonik Industries AG, especially the 47, 48, 61, 61LV, 77, 80, 81 products); Geniosil® STP (from Wacker Chemie AG; especially the E10, E15, E30, E35 products).

Particularly preferred organic polymers having silane groups have end groups of the formula (IX)

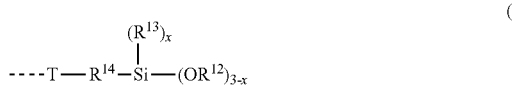

(IX)

where $R^{14}$ is a divalent linear or branched hydrocarbyl radical which has 1 to 12 carbon atoms and optionally has cyclic and/or aromatic moieties and optionally one or more heteroatoms, especially one or more nitrogen atoms, T is a divalent radical selected from —O—, —S—, —N($R^{15}$)—,
—O—CO—N($R^{15}$)—, —N($R^{15}$)—CO—O— and —N($R^{15}$)—CO—N($R^{15}$)—, where $R^{15}$ is a hydrogen radical or a linear or branched hydrocarbyl radical having 1 to 20 carbon atoms which optionally has cyclic moieties and which optionally has an alkoxysilane, ether or carboxylic ester group, and $R^{12}$, $R^{13}$ and x are as defined above.

It is preferable when $R^{14}$ is 1,3-propylene or 1,4-butylene, wherein butylene may be substituted by one or two methyl groups.

It is particularly preferable when $R^{14}$ is 1,3-propylene.

Preferably, the compound containing at least one hexahydrotriazine unit of the formula (I) is present in the curable composition in such an amount that the concentration of amidine and/or guanidine groups based on the amount of the functional polymer is in the range from 0.1 to 50 mmol/100 g, preferably 0.2 to 50 mmol/100 g, especially 0.5 to 20 mmol/100 g.

Such a composition has good storability and rapid curing.

In addition to the compound containing at least one hexahydrotriazine unit of the formula (I), the composition may comprise further catalysts which especially catalyze the crosslinking of isocyanate groups and/or silane groups. Suitable further catalysts are especially metal compounds and/or basic nitrogen or phosphorus compounds.

Suitable metal compounds are especially compounds of tin, titanium, zirconium, aluminum or zinc, especially diorganotin(IV) compounds such as in particular dibutyltin(IV) diacetate, dibutyltin(IV) dilaurate, dibutyltin(IV) dineodecanoate or dibutyltin(IV) bis(acetylacetonate) and dioctyltin (IV) dilaurate and also titanium(IV) or zirconium(IV) or aluminum(III) or zinc(II) complexes having in particular alkoxy, carboxylate, 1,3-diketonate, 1,3-ketoesterate or 1,3-ketoamidate ligands.

Suitable basic nitrogen or phosphorus compounds are especially imidazoles, pyridines, phosphazene bases or preferably amines, further hexahydrotriazines, biguanides, further guanidines or further amidines.

Suitable amines are, in particular, alkyl-, cycloalkyl- or aralkylamines such as triethylamine, triisopropylamine, 1-butylamine, 2-butylamine, tert-butylamine, 3-methyl-1-butylamine, 3-methyl-2-butylamine, dibutylamine, tributylamine, hexylamine, dihexylamine, cyclohexylamine, dicyclohexylamine, dimethylcyclohexylamine, benzylamine, dibenzylamine, dimethylbenzylamine, octylamine, 2-ethylhexylamine, di-(2-ethylhexyl)amine, laurylamine, N,N-dimethyllaurylamine, stearylamine, N,N-dimethylstearylamine; fatty amines derived from natural fatty acid mixtures; aliphatic, cycloaliphatic or araliphatic diamines such as ethylenediamine, butanediamine, hexamethylenediamine, dodecanediamine, neopentanediamine, 2-methylpentamethylenediamine (MPMD), 2,2(4),4-trimethylhexamethylenediamine (TMD), isophoronediamine (IPD), 2,5(2,6)-bis(aminomethyl)bicyclo[2.2.1]heptane (NBDA), xylylene-1,3-diamine (MXDA), N,N'-di(tert-butyl)ethylenediamine, N,N,N',N'-tetramethylethylenediamine, N,N,N',N'-tetramethylpropylenediamine, N,N,N',N'-tetramethylhexamethylenediamine, 3-(dimethylamino)propylamine, 3-(methylamino)propylamine, 3-(cyclohexylamino)propylamine, piperazine, N-methylpiperazine, N,N'-dimethylpiperazine, 1,4-diazabicyclo[2.2.2]octane (DABCO), fatty polyamines such as N-cocoalkylpropane-1,3-diamine; polyalkyleneamines such as diethylenetriamine, dipropylenetriamine, triethylenetetramine (TETA), tetraethylenepentamine (TEPA), pentamethylenehexamine (PEHA), 3-(2-aminoethyl)aminopropylamine, N,N'-bis(3-aminopropyl)ethylenediamine, N-(3-aminopropyl)-N-methylpropanediamine, bis(3-dimethylaminopropyl)amine, N-(3-dimethylaminopropyl)propylene-1,3-diamine, N-(2-aminoethyl)piperazine (N-AEP), N-(2-aminopropyl)piperazine, N,N'-di-(2-aminoethyl)piperazine, 1-methyl-4-(2-dimethylaminoethyl)piperazine, N,N,N',N'',N''-pentamethyldiethylenetriamine, N,N,N',N'', N''-pentamethyldipropylenetriamine, polyethyleneimines obtainable for example under the trade names Lupasol® (from BASF) and Epomin® (from Nippon Shokubai); ether amines, such as, in particular, 2-methoxyethylamine, 2-ethoxyethylamine, 3-methoxypropylamine, 3-ethoxypropylamine, 3-(2-ethylhexyloxy)propylamine, 3-(2-methoxyethoxy)propylamine, morpholine, N-methylmorpholine, N-ethylmorpholine, 2-aminoethylmorpholine, bis(2-aminoethyl) ether, bis(dimethylaminoethyl) ether, bis(dimorpholinoethyl) ether (DMDEE), N,N,N'-trimethyl-N'-hydroxyethylbis(2-aminoethyl) ether, 3,6-dioxaoctane-1,8-diamine, 4,7-dioxadecane-1,10-diamine, 4,7-dioxadecane-2,9-diamine, 4,9-dioxadodecane-1,12-diamine, 5,8-dioxadodecane-3,10-diamine, 4,7,10-trioxatridecane-1,13-diamine, or 2-aminopropyl-terminated glycols, of the kind obtainable for example under the trade name Jeffamine® (from Huntsman); amino alcohols, such as, in particular, ethanolamine, isopropanolamine, diethanolamine, diisopropanolamine, triethanolamine, triisopropanolamine, N-butylethanolamine, diglycolamine, N,N-diethylethanolamine, N-methyldiethanolamine, N-methyldiisopropylamine, N,N,N'-trimethylaminoethylethanolamine, N-(3-dimethylaminopropyl)-N,N-diisopropanolamine, N,N-bis(3-dimethylaminopropyl)-N-isopropanolamine, 2-(2-dimethylaminoethoxy) ethanolamine, or adducts of mono- and polyamines with epoxides or diepoxides; amines containing phenol groups, such as, in particular, condensation products of phenols, aldehydes, and amines (called Mannich bases and phenalkamines) such as, in particular, 2-(dimethylaminomethyl)phenol, 2,4,6-tris(dimethylaminomethyl)phenol, or polymers of phenol, formaldehyde, and N,N-dimethylpropane-1,3-diamine, and also phenalkamines obtainable commercially under the brand names Cardolite® (from Cardolite), Aradur® (from Huntsman), and Beckopox® (from Cytec); polyamines containing amide groups, so-called polyamidoamines, of the kind available commercially, for example, under the brand names Versamid® (from Cognis), Aradur® (from Huntsman), Euretek® (from Huntsman) or Beckopox® (from Cytec); or aminosilanes, such as, in particular, 3-aminopropyltrimethoxysilane, 3-aminopropyldimethoxymethylsilane, N-(2-aminoethyl)-3-aminopropyltrimethoxysilane, N-(2-aminoethyl)-3-aminopropyl-methyldimethoxysilane, N-(2-aminoethyl)-N'-[3-(trimethoxysilyl) propyl]ethylenediamine or their analogs with ethoxy in place of the methoxy groups on the silicon atom.

Suitable further hexahydrotriazines are especially 1,3,5-hexahydrotriazine, 1,3,5-trimethylhexahydrotriazine or 1,3,5-tris(3-(dimethylamino)propyl)hexahydrotriazine.

Suitable biguanides are especially biguanide, 1-butylbiguanide, 1,1-dimethylbiguanide, 1-butylbiguanide, 1-phenylbiguanide or 1-(o-tolyl)biguanide (OTBG).

Suitable further guanidines are especially 1-butylguanidine, 1,1-dimethylguanidine, 1,3-dimethylguanidine, 1,1,3,3-tetramethylguanidine (TMG), 2-(3-(trimethoxysilyl)propyl)-1,1,3,3-tetramethylguanidine, 2-(3-(methyldimethoxysilyl)propyl)-1,1,3,3-tetramethylguanidine, 2-(3-(triethoxysilyl)propyl)-1,1,3,3-tetramethylguanidine, 1,5,7-triazabicyclo-[4.4.0]dec-5-ene (TBD), 7-methyl-1,5,7-triazabicyclo[4.4.0]dec-5-ene, 7-cyclohexyl-1,5,7-triazabicyclo[4.4.0]dec-5-ene, 1-phenylguanidine, 1-(o-tolyl)guanidine (OTG), 1,3-diphenylguanidine, 1,3-di(o-tolyl)guanidine or 2-guanidinobenzimidazole.

Suitable further amidines are especially 1,8-diazabicyclo[5.4.0]undec-7-ene (DBU), 1,5-diazabicyclo[4.3.0]non-5-ene (DBN), 6-dibutylamino-1,8-diaza-bicyclo[5.4.0]undec-7-ene, 6-dibutylamino-1,8-diazabicyclo[5.4.0]undec-7-ene, N,N'-di-n-hexylacetamidine (DHA), 2-methyl-1,4,5,6-tetrahydropyrimidine, 1,2-dimethyl-1,4,5,6-tetrahydropyrimidine, 2,5,5-trimethyl-1,4,5,6-tetrahydropyrimidine, N-(3-trimethoxysilylpropyl)-4,5-dihydroimidazole or N-(3-triethoxysilylpropyl)-4,5-dihydroimidazole.

In addition, the composition may comprise, as cocatalyst, an acid, especially a carboxylic acid. Preference is given to aliphatic carboxylic acids such as formic acid, lauric acid, stearic acid, isostearic acid, oleic acid, 2-ethyl-2,5-dimethylcaproic acid, 2-ethylhexanoic acid, neodecanoic acid, fatty acid mixtures from the hydrolysis of natural fats and oils or di- and polycarboxylic acids, especially poly(meth)acrylic acids.

In a preferred embodiment, the composition is essentially free of organotin compounds. Organotin-free compositions are advantageous in terms of protection of health and protection of the environment. More particularly, the tin content of the curable composition is less than 0.1% by weight, especially less than 0.05% by weight.

In a further preferred embodiment, the composition comprises a combination of at least one compound containing at least one hexahydrotriazine unit of the formula (I) and at least one organotin compound, especially a diorganotin(IV) compound such as those mentioned above. Such a composition has a high curing rate even in the case of a low tin content, which is advantageous for toxicological and environmental reasons.

In one embodiment, the composition additionally comprises, as well as the compound containing at least one hexahydrotriazine unit of the formula (I), at least one organotitanate. A combination of a compound containing at least one hexahydrotriazine unit of the formula (I) and an organotitanate has particularly high catalytic activity. This enables rapid curing with a comparatively small use amount of organotitanate.

Suitable organotitanates are especially titanium(IV) complexes.

Preferred organotitanates are especially selected from titanium(IV) complexes having two 1,3-diketonate ligands, especially 2,4-pentanedionate (=acetylacetonate), and two alkoxide ligands;

titanium(IV) complexes having two 1,3-ketoesterate ligands, especially ethylacetoacetate, and two alkoxide ligands;

titanium(IV) complexes having one or more aminoalkoxide ligands, especially triethanolamine or 2-((2-aminoethyl)amino)ethanol, and one or more alkoxide ligands;

titanium(IV) complexes having four alkoxide ligands (orthotitanates);

and more highly condensed organotitanates, especially oligomeric titanium(IV) tetrabutoxide, also referred to as polybutyl titanate;

where suitable alkoxide ligands are especially isobutoxy, n-butoxy, isopropoxy, ethoxy and 2-ethylhexoxy.

Especially suitable are the commercially available products Tyzor® AA, GBA, GBO, AA-75, AA-65, AA-105, DC, BEAT, BTP, TE, TnBT, KTM, TOT, TPT or IBAY (all from Dorf Ketal); Tytan PBT, TET, X85, TAA, ET, S2, S4 or S6 (all from Borica Company Ltd.) and Ken-React® KR® TTS, 7, 9QS, 12, 26S, 33DS, 38S, 39DS, 44, 134S, 138S, 133DS, 158FS or LICA® 44 (all from Kenrich Petrochemicals).

Very particularly suitable organotitanates are selected from bis(ethylacetoacetato)diisobutoxytitanium(IV) (commercially available, for example, as Tyzor® IBAY from Dorf Ketal), bis(ethylacetoacetato)diisopropoxytitanium (IV) (commercially available, for example, as Tyzor® DC from Dorf Ketal), bis(acetylacetonato)diisopropoxytitanium (IV), bis(acetylacetonato)diisobutoxytitanium(IV), tris(oxyethyl)amineisopropoxytitanium(IV), bis[tris(oxyethyl) amine]diisopropoxytitanium(IV), bis(2-ethylhexane-1,3-dioxy)titanium(IV), tris[2-((2-aminoethyl)amino)ethoxy] ethoxytitanium(IV), bis(neopentyl(diallyl)oxy) diethoxytitanium(IV), tetra(isopropoxy)titanate, tetra(n-butoxy)titanate, tetra(2-ethylhexyloxy)titanate and polybutyl titanate.

Most preferred are bis(ethylacetoacetato)diisobutoxytitanium(IV) or bis(ethylacetoacetato)diisopropoxytitanium (IV).

The curable composition preferably comprises at least one further constituent selected from the group consisting of fillers, plasticizers, rheology additives, desiccants, adhesion promoters and crosslinkers. More preferably, it comprises any combination of two or more of these constituents.

Suitable fillers are especially inorganic or organic fillers, especially natural, ground or precipitated calcium carbonates, optionally coated with fatty acids, especially stearic acid, baryte (heavy spar), talcs, quartz flours, quartz sand, dolomites, wollastonites, kaolins, calcined kaolins, mica (potassium aluminum silicate), molecular sieves, aluminum oxides, aluminum hydroxides, magnesium hydroxide, silicas including finely divided silicas from pyrolysis processes, industrially produced carbon blacks, graphite, metal powders such as aluminum, copper, iron, silver or steel, PVC powder or hollow spheres.

Suitable plasticizers are especially trialkylsilyl-terminated polydialkylsiloxanes, preferably trimethylsilyl-terminated polydimethylsiloxanes, especially having viscosities in the range from 10 to 1,000 mPa·s, or corresponding compounds in which some of the methyl groups have been replaced by other organic groups, especially phenyl, vinyl or trifluoropropyl groups, called reactive plasticizers, in the form of monofunctional polysiloxanes, i.e. those that are reactive at one end, carboxylic esters such as phthalates, especially dioctyl phthalate, bis(2-ethylhexyl) phthalate, bis (3-propylheptyl) phthalate, diisononyl phthalate or diisodecyl phthalate, diesters of ortho-cyclohexane-dicarboxylic acid, especially diisononyl 1,2-cyclohexanedicarboxylate, adipates, especially dioctyl adipate, bis(2-ethylhexyl) adipate, azelates, especially bis(2-ethylhexyl) azelate, sebacates, especially bis(2-ethylhexyl) sebacate or diisononyl sebacate, polyols, especially polyoxyalkylene polyols or polyester polyols, glycol ethers, glycol esters, organic phosphoric or sulfonic esters, sulfonamides, polybutenes, or fatty acid methyl or ethyl esters derived from natural fats or oils, also called "biodiesel", plasticizers containing siloxane groups being particularly suitable for polymers having silane groups in the form of polyorganosiloxanes.

Suitable rheology additives are especially thickeners, especially sheet silicates such as bentonites, derivatives of castor oil, hydrogenated castor oil, polyamides, polyurethanes, urea compounds, fumed silicas, cellulose ethers or hydrophobically modified polyoxyethylenes.

Suitable desiccants are especially tetraethoxysilane, vinyltrimethoxysilane, vinyltriethoxysilane or organoalkoxysilanes which have a functional group in the α position to the silane group, especially N-(methyldimethoxysilylmethyl)-O-methylcarbamate, (methacryloyloxymethyl)silanes, methoxymethylsilanes, orthoformic esters, calcium oxide, molecular sieves, highly reactive isocyanates such as p-tosyl isocyanate, monomeric diisocyanates or monooxazolidines such as Incozol® 2 (from Incorez), especially vinyltrimethoxysilane or vinyltriethoxysilane.

Suitable adhesion promoters and/or crosslinkers are especially aminosilanes such as, in particular, 3-aminopropyltrimethoxysilane, 3-aminopropyldimethoxymethylsilane, N-(2-aminoethyl)-3-aminopropyltrimethoxysilane, N-(2-aminoethyl)-3-aminopropyldimethoxymethylsilane, N-(2-aminoethyl)-N'-[3-(trimethoxysilyl)propyl]ethylenediamine or the analogs thereof with ethoxy in place of methoxy groups, and also N-phenyl-, N-cyclohexyl- or N-alkylaminosilanes, mercaptosilanes, epoxysilanes, (meth)acrylosilanes, anhydridosilanes, carbamatosilanes, alkylsilanes or iminosilanes, oligomeric forms of these silanes, adducts formed from primary aminosilanes with epoxysilanes or (meth)acrylosilanes or anhydridosilanes, amino-functional alkylsilsesquioxanes, especially amino-functional methylsilsesquioxane or amino-functional propylsilsesquioxane. Especially suitable are 3-aminopropyltrimethoxysilane, 3-aminopropyltriethoxysilane, N-(2-aminoethyl)-3-aminopropyltrimethoxysilane, N-(2-aminoethyl)-3-aminopropyltriethoxysilane, 3-glycidoxypropyltrimethoxysilane, 3-glycidoxypropyltriethoxysilane or 3-ureidopropyltrimethoxysilane, or oligomeric forms of these silanes;

In a preferred embodiment, the composition comprises at least one desiccant and at least one adhesion promoter and/or crosslinker.

In a preferred embodiment, the composition does not comprise any phthalates as plasticizers. Such compositions are toxicologically advantageous and in some cases have fewer problems with migration effects.

If the composition comprises a polyisocyanate and/or a polyurethane polymer having isocyanate groups, additionally preferably, at least one polyfunctional compound reactive toward isocyanate groups is present, such as, in particular, one or more polyols, especially the polyols mentioned as being suitable for the preparation of a polyurethane polymer having isocyanate groups. Preference is given to polyether polyols, polyester polyols, polycarbonate polyols, poly(meth)acrylate polyols or polybutadiene polyols. Particular preference is given to polyether polyols, especially polyoxypropylene polyols and/or ethylene oxide-terminated polyoxypropylene polyols. Preference is given to polyols having an average molecular weight in the range from 400 to 10,000 g/mol, especially 500 to 6,000 g/mol. Preference is given to polyols having an average OH functionality in the range from 1.6 to 4, especially 1.8 to 3, more preferably 2.2 to 3. Likewise suitable are polyether polyols with polymer particles dispersed therein, especially those with styrene-acrylonitrile particles (SAN) or polyurea or polyhydrazodicarbonamide particles (PHD).

chain extenders, especially ethane-1,2-diol, propane-1,3-diol, 2-methylpropane-1,3-diol, butane-1,4-diol, pentane-1,5-diol, neopentyl glycol, hexane-1,6-diol, 3-methylpentane-1,5-diol, heptane-1,7-diol, octane-1,8-diol, cyclohexane-1,3-dimethanol, cyclohexane-1,4-dimethanol, diethylene glycol or triethylene glycol;

amino alcohols, especially 2-aminoethanol, 2-(2-aminoethoxy)ethanol or 3-aminomethyl-3,5,5-trimethylcyclohexanol or derivatives thereof that have ether, ester or urethane groups;

compounds having blocked amino groups, especially aldimines, ketimines, enamines, oxazolidines, imidazolidines or hexahydropyrimidines;

or polyamines.

The composition may contain further constituents, especially the following auxiliaries and admixtures:

pigments, especially titanium dioxide or iron oxides;

dyes;

stabilizers against oxidation, heat, light or UV radiation;

natural resins, fats or oils such as rosin, shellac, linseed oil, castor oil or soya oil;

non-reactive polymers such as, in particular, homo- or copolymers of unsaturated monomers, especially from the group comprising ethylene, propylene, butylene, isobutylene, isoprene, vinyl acetate or alkyl (meth) acrylates, especially polyethylenes (PE), polypropylenes (PP), polyisobutylenes, ethylene-vinyl acetate copolymers (EVA) or atactic poly-α-olefins (APAO);

flame-retardant substances, especially the already mentioned fillers aluminum hydroxide and magnesium hydroxide, or, in particular, organic phosphoric esters such as, in particular, triethyl phosphate, tricresyl phosphate, triphenyl phosphate, diphenyl cresyl phosphate, isodecyl diphenyl phosphate, tris(1,3-dichloro-2-propyl) phosphate, tris(2-chloroethyl) phosphate, tris(2-ethylhexyl) phosphate, tris(chloroisopropyl) phosphate, tris(chloropropyl) phosphate, isopropylated triphenyl phosphate, mono-, bis- or tris(isopropylphenyl) phosphates of different degrees of isopropylation, resorcinol bis(diphenyl phosphate), bisphenol A bis (diphenyl phosphate) or ammonium polyphosphates;

fibers, especially glass fibers, carbon fibers, metal fibers, ceramic fibers or polymer fibers such as polyamide fibers or polyethylene fibers;

surface-active substances, especially wetting agents, leveling agents, deaerating agents or defoamers;

solvents;

biocides, especially algicides, fungicides or substances that inhibit fungal growth;

and other substances customarily used in curable compositions.

It may be advisable to subject certain constituents to chemical or physical drying before mixing them into the composition.

The composition is preferably produced and stored under exclusion of moisture. It is typically storage-stable with exclusion of moisture in a suitable package or arrangement, such as, in particular, a cartridge, a bottle, a canister, a pouch, a bucket, a hobbock or a vat.

The composition may be in the form of a one-component composition or in the form of a multi-component, especially two-component, composition.

In the present document, "one-component" refers to a composition in which all constituents of the composition are stored in a mixture in the same container and which is curable with moisture.

In the present document, "two-component" refers to a composition in which the constituents of the composition are present in two different components which are stored in separate containers. Only shortly before or during the application of the composition are the two components mixed with one another, whereupon the mixed composition cures, optionally under the action of moisture.

If the composition comprises a polyisocyanate and/or a polyurethane polymer having isocyanate groups, it is preferably a two-component composition. In this case, one component contains the polyisocyanate and/or the polyurethane polymer having isocyanate groups and the other component contains the compound containing at least one hexahydrotriazine unit of the formula (I) and additionally at least one polyfunctional compound reactive toward isocyanate groups.

If the composition comprises an organic polymer having silane groups, it is preferably a one-component composition.

If the composition comprises a polyorganosiloxane having terminal silane groups, it is preferably a one-component composition, also referred to as RTV-1, or a two-component composition, also referred to as RTV-2. In the case of an RTV-2 composition, the polyorganosiloxane having terminal silane groups is preferably a constituent of the first component, and a silane crosslinker, especially a silane of the formula (VIII), is preferably a constituent of the second component. The compound containing at least one hexahydrotriazine unit of the formula (I) may be present here in the first and/or in the second component.

Any second or optionally further components is/are mixed with the first component prior to or during application, especially by means of a static mixer or by means of a dynamic mixer.

The composition is especially applied at ambient temperature, preferably within a temperature range between 0° C. and 45° C., especially 5° C. to 35° C., and also cures under these conditions.

On application, the crosslinking reaction of the functional groups commences, if appropriate under the influence of moisture.

Isocyanate groups present react with hydroxyl groups, or primary or secondary amino groups, or under the influence of moisture with blocked amino groups. Any further isocyanate groups present react with one another under the influence of moisture.

Silane groups present can condense with silanol groups present to afford siloxane groups (Si—O—Si groups). Silane groups present can also be hydrolyzed on contact with moisture to give silanol groups (Si—OH groups) and can form siloxane groups (Si—O—Si groups) through subsequent condensation reactions.

As a result of these reactions, the composition ultimately cures. The compound containing at least one hexahydrotriazine unit of the formula (I) accelerates this curing.

If water is required for the curing, this can either come from the air (atmospheric humidity), or else the composition can be contacted with a water-containing component, for example by painting, for example with a smoothing agent, or by spraying, or water or a water-containing component can be added to the composition on application, for example in the form of a water-containing or water-releasing liquid or paste. A paste is especially suitable if the composition itself is in the form of a paste.

In the case of curing by means of atmospheric humidity, the composition cures from the outside inward, at first forming a skin on the surface of the composition. The so-called skin time is a measure of the curing rate of the composition. The speed of curing is generally determined by various factors, for example the availability of water, the temperature, etc.

The composition is suitable for a multitude of uses, especially as a paint, varnish or primer, as a resin for production of fiber composites, as a rigid foam, flexible foam, molding, elastomer, fiber, film or membrane, as a potting compound, sealant, adhesive, covering, coating or paint for construction and industrial applications, for example as a seam seal, cavity seal, electrical insulation compound, spackling compound, joint sealant, weld or crimp seam sealant, assembly adhesive, bodywork adhesive, glazing adhesive, sandwich element adhesive, laminating adhesive, laminate adhesive, packaging adhesive, wood adhesive, parquet adhesive, anchoring adhesive, floor covering, floor coating, balcony coating, roof coating, concrete protection coating, parking garage coating, seal, pipe coating, anticorrosion coating, textile coating, damping element, sealing element or spackling compound.

The composition is particularly suitable as an adhesive and/or sealant, especially for joint sealing and for elastic adhesive bonds in construction and industrial applications, or as elastic coating with crack-bridging properties, especially for protection and/or sealing of, for example, roofs, floors, balconies, parking decks or concrete pipes.

The composition is thus preferably an adhesive or a sealant or a coating. A composition of this kind typically comprises fillers, plasticizers, desiccants, adhesion promoters and/or crosslinkers and optionally further auxiliaries and additives.

For use as an adhesive or sealant the composition preferably has a pasty consistency with pseudoplastic properties. A pasty sealant or adhesive of this kind is especially applied to a substrate from standard cartridges which are operated manually, with compressed air or with a battery, or from a vat or hobbock via a delivery pump or an extruder, optionally via an application robot. For use as a coating the composition preferably has a liquid consistency at room temperature with self-leveling properties. It may be slightly thixotropic, such that the coating is applicable to inclined to vertical surfaces without flowing away immediately. It is especially applied by means of a roller or brush or by pouring-out and distribution by means, for example, of a roller, a scraper or a notched trowel.

During application the composition is preferably applied to at least one substrate.

Suitable substrates are especially glass, glass ceramic, concrete, mortar, brick, tile, gypsum and natural rocks such as limestone, granite or marble;

metals and alloys such as aluminum, iron, steel or non-ferrous metals, and also surface-finished metals or alloys such as galvanized or chromed metals;

leather, textiles, paper, wood, wood-based materials bonded with resins, for example phenolic, melamine or epoxy resins, resin-textile composites and further polymer composites;

plastics such as polyvinyl chloride (rigid and flexible PVC), acrylonitrile-butadiene-styrene copolymers (ABS), polycarbonate (PC), polyamide (PA), polyesters, poly(methyl methacrylate) (PMMA), epoxy resins, polyurethanes (PUR), polyoxymethylene (POM), polyolefins (PO), polyethylene (PE) or polypropylene (PP), ethylene/propylene copolymers (EPM) and ethylene/propylene/diene terpolymers (EPDM), and fiber-reinforced plastics such as carbon fiber-reinforced plastics (CFP), glass fiber-reinforced plastics (GFP) and sheet molding compounds (SMC), where the plastics may preferably have been surface-treated by means of plasma, corona or flames;

coated substrates such as powder-coated metals;

paints or varnishes, especially automotive topcoats, metal paints, furniture varnishes or wood varnishes.

If required, the substrates can be pretreated prior to the application of the composition, especially by physical and/or chemical cleaning methods or by the application of an adhesion promoter, an adhesion promoter solution or a primer.

The composition is particularly suitable for contact with substrates that are particularly sensitive to defects caused by migrating substances, especially by the formation of discoloration or specks. These are, in particular, fine-pore substrates such as marble, limestone or other natural stones, gypsum, cement mortar or concrete, but also plastics. Especially on PVC, severe discoloration is observed in the presence of catalysts, for example DBU or TMG, and cannot be removed by cleaning. No such effects are observed with the compound containing at least one hexahydrotriazine unit of the formula (I).

It is possible to bond or seal two identical or two different substrates, especially the aforementioned substrates.

After the curing of the composition, a cured composition is obtained.

The use of the composition affords an article which has in particular been bonded, sealed or coated with the composition. The article is especially a built structure, especially a structure built by structural engineering or civil engineering, an industrially manufactured item or a consumable item, especially a window, a domestic appliance or a means of transport such as in particular an automobile, a bus, a truck, a rail vehicle, a ship, an aircraft or a helicopter; or the article may be an installable component thereof.

EXAMPLES

Working examples are adduced hereinafter, which are intended to elucidate the invention described in detail. It will be appreciated that the invention is not restricted to these described working examples.

"Standard climatic conditions" refer to a temperature of 23±1° C. and a relative air humidity of 50±5%.

$^1$H and $^{13}$C NMR spectra were measured at room temperature on a spectrometer of the Bruker Ascend type at 400.14 MHz ($_1$H) or 100.63 MHz ($^{13}$C); the chemical shifts δ are reported in ppm relative to tetramethylsilane (TMS). Coupling constants J are reported in Hz. No distinction was made between true coupling and pseudo-coupling patterns.

Infrared spectra (FT-IR) were measured on a Nicolet iS5 FT-IR instrument from Thermo Scientific equipped with a horizontal ATR measurement unit with a diamond crystal. Liquid samples were applied undiluted as films; solid samples were dissolved in $CH_2Cl_2$. The absorption bands are reported in wavenumbers ($cm^{-1}$) (measurement window: 4000-650 $cm^{-1}$).

Gas chromatograms (GC) were measured within the temperature range of 60 to 320° C. with a heating rate of 15° C./min and a run time of 10 min at 320° C. The injector temperature was 250° C. A Zebron ZB-5 column was used (L=30 m, ID=0.25 mm, dj=0.5 μm) with a gas flow rate of 1.5 ml/min. Detection was effected by means of flame ionization (FID), with evaluation of the signals via the area percent method.

The skin time (HBZ) was determined by applying a few grams of the composition to cardboard in a film thickness of about 2 mm and measuring under standard climatic conditions the time until, upon gentle tapping of the surface of the composition using an LDPE pipette, no residue remained on the pipette for the first time.

The characteristics of the surface were tested by touch.

The mechanical properties of tensile strength, elongation at break and modulus of elasticity (at 0-25% or at 0-5% and 0-50% elongation) were measured in accordance with DIN EN 53504 at a pulling speed of 200 mm/min.

Viscosity was measured on a thermostated Rheotec RC30 cone-plate viscometer (cone diameter 50 mm, cone angle 1°, cone tip-plate distance 0.05 mm, shear rate 10 rpm).

Commercial Substances Used:

Jeffamine® D-230 (Huntsman), polyoxypropylenediamine having an average molecular weight of about 240 g/mol, amine value 465 mg KOH/g Jeffamine® D-400 (Huntsman), polyoxypropylenediamine having an average molecular weight of about 400 g/mol, amine value 247 mg KOH/g Wacker® Fluid NH 15 D (Wacker), α,ω-bis(3-aminopropyl)poly(dimethylsiloxane) having an average molecular weight of about 1050 g/mol, amine value 106 mg KOH/g Shin-Etsu Silicone® KF-8010 (Shin Etsu), α,ω-bis(3-aminopropyl)poly(dimethylsiloxane) having an average molecular weight of about 860 g/mol Wacker® Aminöl 446011-20 VP (Wacker), α-(3-aminopropyl)-ω-isobutoxypoly(dimethylsiloxane) having an average molecular weight of about 1650 g/mol, amine value 34 mg KOH/g 1,3-diaminopropane (Sigma-Aldrich)

bis(3-aminopropyl)amine (Baxxodur® EC 110 from BASF)

n-hexylamine (Sigma-Aldrich)

isopropylamine (Sigma-Aldrich)

3-dimethylamino-1-propylamine (Sigma-Aldrich)

N,N'-dicyclohexylcarbodiimide (Sigma-Aldrich)

n-propylamine (Sigma-Aldrich)

3-aminopropyltriethoxysilane (AMEO) (Sigma-Aldrich)

trimethyl orthoacetate (Sigma-Aldrich)

lanthanum(III) trifluoromethanesulfonate (Sigma-Aldrich)

Poly bd® R-45HTLO (Cray Valley), polybutadienepolyol with OH functionality about 2.5, average molecular weight about 2800 g/mol and OH number 47.1 mg KOH/g Desmodur® CD (Covestro), modified diphenylmethane diisocyanate containing MDI-carbodiimide adducts, liquid at room temperature, 28% by weight of NCO Preparation of Amino Amidines or Guanidines of the formula $H_2N$-A-Z:

Amidine A1: 1-(3-aminopropyl)-2-methyl-1,4,5,6-tetrahydropyrimidine

In a round-bottom flask, 62.97 g of trimethyl orthoacetate, 62.12 g of bis(3-aminopropyl)amine and 2.80 g of lanthanum(III) trifluoromethanesulfonate were mixed under a nitrogen atmosphere, and the mixture was heated to 120° C. while stirring at reflux for 3 days. Thereafter, the reaction mixture was freed of the volatile constituents under reduced pressure and the residue was distilled under reduced pressure. This gave 26.65 g of a colorless oil having a boiling temperature of 85-88° C. at 0.1 mbar, which, according to the GC spectrum, contained a content of 87% amidine A1.

$^1$H NMR (CDCl$_3$) (signals of amidine A1 only): δ 1.05 (s, 2 H, NH$_2$), 1.57-1.70 (m, 2 H, CH$_2$CH$_2$NH$_2$), 1.74-1.86 (m, 2 H, C═NCH$_2$CH$_2$), 1.97 (s, 3 H, CH$_3$), 2.60-2.80 (m, 2 H, CH$_2$CH$_2$NH$_2$), 3.10-3.24 and 3.25-3.34 (2×m, 4H and 2 H, CH$_2$N).

$^{13}$C NMR (CDCl$_3$): δ 22.02 (CH$_2$), 22.56 (CH$_3$), 32.10 (CH$_2$), 39.44 (CH$_2$), 44.50 (CH$_2$), 45.93 (CH$_2$), 49.09 (CH$_2$), 154.89 (C).

FT-IR: 3260, 2924, 2748, 1611, 1482, 1433, 1375, 1353, 1317, 1289, 1211, 1149, 1126, 1099, 1085, 1031, 1014, 942, 879, 821, 752, 735, 692.

Guanidine G1: Reaction product comprising 1-(3-aminopropyl)-2,3-dicyclohexylguanidine In a round-bottom flask, 2.50 g of 1,3-diaminopropane and 6.89 g of N,N'-dicyclohexylcarbodiimide were mixed under a nitrogen atmosphere and the mixture was heated to 120° C. while stirring. At regular intervals, the reaction mixture was analyzed by means of FT-IR spectroscopy. After 1 hour, the carbodiimide band at about 2120 cm$^{-1}$ had disappeared completely. Thereafter, the reaction mixture was freed of the volatile constituents under reduced pressure. This gave 9.36 g of a pale yellow oil.

$^1$H NMR (CDCl$_3$): δ 1.05-1.2 and 1.25-1.40 (2×m, 10 H), 1.54-1.78 (m, 10 H), 1.88-2.0 (m, 4 H), 2.73 (m, 2 H), 3.12 (m, 2 H), 3.22 (br s, 2 H).

$^{13}$C NMR (CDCl$_3$): δ 24.75 and 24.89 and 25.0 (CH$_2$), 25.47 (CH$_2$), 32.20 (CH$_2$), 33.88 (CH$_2$), 39.9 (CH$_2$NH), 41.94 (CH$_2$NH$_2$), 50.95 (CH), 151.5 (C).

FT-IR: 3371 (N—H), 2921, 2849, 1627 (C═N), 1502, 1447, 1324, 1238, 1147, 1111, 888, 713.

Guanidine G2: reaction product containing 1-(ω-3-aminopropyl-α-1,3-propylenepoly(dimethylsiloxane))-2,3-dicyclohexylguanidine with an average molecular weight of about 1,260 g/mol In a round-bottom flask, 30.23 g of Wacker® Fluid NH 15 D and 6.00 g of N,N'-dicyclohexylcarbodiimide were mixed under a nitrogen atmosphere and the mixture was heated to 115° C. while stirring. At regular intervals, the reaction mixture was analyzed by means of FT-IR spectroscopy. After 2 hours, the carbodiimide band at about 2120 cm$^{-1}$ had disappeared completely. This gave a yellowish oil.

$^1$H NMR (CDCl$_3$): δ 0.0 (s, 88 H, CH$_3$Si), 0.41-0.53 (m, 4 H, CH$_2$—Si), 1.05-1.18 and 1.20-1.30 (2×m, 10 H), 1.33-1.5 (m, 6 H, CH$_2$), 1.6-1.78 (m, 4 H), 1.88-2.0 (m, 4 H), 2.57 (t, 2 H, J=7 Hz, CH$_2$—NH$_2$), 2.92 (t, 2 H, J=7.2 Hz, CH$_2$—NH), 3.13 (br s, 2 H, CH—N).

$^{13}$C NMR (CDCl$_3$): δ 0.13 and 0.16 and 0.37 (CH$_3$Si), 14.89 and 14.23 (CH$_2$), 23.85 and 23.91 (CH$_2$), 24.87 (CH$_2$), 33.28 (CH$_2$), 44.16 (CH$_2$), 47.2 (CH$_2$), 50.45 (CH), 150.0 (C).

FT-IR: 2960, 2927, 2853, 1645, 1496, 1449, 1411, 1361, 1257, 1013, 789, 700.

Guanidine G3: reaction product containing 1-(ω-3-aminopropyl-α-1,3-propylenepoly(dimethylsiloxane))-2,3-dicyclohexylguanidine with an average molecular weight of about 1,070 g/mol In a round-bottom flask, 27.29 g of Shin-Etsu Silicone® KF-8010 and 6.66 g of N,N'-dicyclohexylcarbodiimide were mixed under a nitrogen atmosphere and the mixture was heated to 115° C. while stirring. At regular intervals, the reaction mixture was analyzed by means of FT-IR spectroscopy. After 2 hours, the carbodiimide band at about 2120 cm$^{-1}$ had disappeared completely. This gave a yellowish oil.

$^1$H NMR (CDCl$_3$): δ 0.0 (s, 88 H, CH$_3$Si), 0.41-0.53 (m, 4 H, CH$_2$—Si), 1.0-1.16 and 1.16-1.30 (2×m, 10 H), 1.3-1.58 (m, 6 H, CH$_2$), 1.58-1.78 (m, 4 H), 1.88-2.0 (m, 4 H), 2.51-2.60 (m, 2 H, CH$_2$), 2.86-2.95 (m, 2 H, CH$_2$), 3.13 (br s, 2 H, CH).

$^{13}$C NMR (CDCl$_3$): δ 0.13 and 0.16 and 0.37 (CH$_3$Si), 14.24 and 14.91 (CH$_2$—Si), 24.26 (CH$_2$), 24.90 (CH$_2$), 26.57 (CH$_2$), 33.44 (CH$_2$), 44.18 (CH$_2$), 47.25 (CH$_2$), 50.38 (CH), 150.0 (C).

FT-IR: 2959, 2927, 2854, 1644 (C═N), 1450, 1412, 1257, 1015, 837, 789, 702.

Guanidine G4: reaction product containing 1-(ω-aminopropylpolyoxypropylene)-2,3-dicyclohexylguanidine with an average molecular weight of about 450 g/mol In a round-bottom flask, 24.97 g of Jeffamine® D-230 and 20.94 g of N,N'-dicyclohexylcarbodiimide were mixed under a nitrogen atmosphere and the mixture was heated to 115° C. while stirring. At regular intervals, the reaction mixture was analyzed by means of FT-IR spectroscopy. After 4 hours, the carbodiimide band at about 2120 cm$^{-1}$ had disappeared completely. This gave a yellowish oil.

$^{13}$C NMR (CDCl$_3$): 17.1-17.4 (multiple CH$_3$), 19.66 (CH$_3$), 25.02 and 25.14 (CH$_2$), 25.84 (CH$_2$), 26.57 (CH$_2$), 34.09 and 34.40 (multiple CH$_2$), 46.23 and 46.76 (CH-cy), 49.9 (CH—N), 51.6 (CH—NH$_2$), 74.26-75.35 (CH$_2$), 76.06-76.26 (CH), 78.08 (CH$_2$).

FT-IR: 3368 (N—H), 2922, 2850, 1637 (C═N), 1498, 1448, 1372, 1337, 1283, 1237, 1103, 1026, 977, 888, 860, 826, 718.

Guanidine G5: reaction product containing 1-(ω-aminopropylpolyoxypropylene)-2,3-dicyclohexylguanidine with an average molecular weight of about 650 g/mol In a round-bottom flask, 24.31 g of Jeffamine® D-400 and 11.46 g of N,N'-dicyclohexylcarbodiimide were mixed under a nitrogen atmosphere and the mixture was heated to 120° C. while stirring for 24 hours. The carbodiimide band at about 2120 cm$^{-1}$ had then disappeared completely. This gave a yellowish oil.

$^{13}$C NMR (CDCL$_3$): 17.1-17.4 (CH$_3$), 19.65 (CH$_3$), 25.02 and 25.14 (CH$_2$), 25.84 (CH$_2$), 34.09 and 34.40 (CH$_2$), 26.57 (CH$_2$), 46.23 and 46.76 (CH-cy), 50.0 (CH—N), 51.6 (CH—NH$_2$), 74.26-75.35 (CH$_2$), 76.06-76.26 (CH), 78.08 (CH$_2$).

FT-IR: 3366 (N—H), 2968, 2925, 2852, 1639 (C═N), 1496, 1448, 1372, 1341, 1256, 1238, 1100, 1018, 924, 888, 860, 826, 714, 666.

Preparation of Hexahydrotriazine Intermediates:

Intermediate HZ-1

In a round-bottom flask, 29.63 g of n-propylamine and 50 mL of n-heptane were mixed under a nitrogen atmosphere, 42.25 g of aqueous formaldehyde solution (37% by weight) were added and the mixture was then stirred at room temperature for 1 hour. The reaction mixture was then washed with 10 mL of water, dried with magnesium sulfate and filtered. Thereafter, the reaction mixture was freed of the volatile constituents under reduced pressure. This gave 35.30 g of an odorless, colorless, very mobile oil.

$^1$H NMR (CDCl$_3$): 0.83 (t, 9 H, J=7.4 Hz, CH$_3$), 1.41 (sext, 6 H, J=7.5 Hz, CH$_2$CH$_3$), 2.30 (t, 6 H, J=7.5 Hz, NCH$_2$CH$_2$), 3.20 (br s, 6 H, NCH$_2$N).

FT-IR: 2957, 2931, 2872, 2783, 1461, 1398, 1375, 1344, 1304, 1272, 1201, 1142, 1114, 1095, 1008, 976, 957, 927, 878, 852, 839, 779, 750.

Intermediate HZ-2

In a round-bottom flask, 4.93 g of intermediate HZ-1 and 5.11 g of 3-aminopropyltriethoxysilane were mixed under a nitrogen atmosphere, the mixture was boiled at reflux at 150° C. for 4 hours and then the volatile constituents were removed under reduced pressure. This gave 8.39 g of an odorless, colorless, mobile oil.

$^1$H NMR (CDCl$_3$): 0.56 (m, 2 H, CH$_2$Si), 0.83 (t, 6 H, J=7.4 Hz, CH$_2$CH$_2$CH$_3$), 1.15 (t, 9 H, J=7.2 Hz, OCH$_2$CH$_3$), 1.42 (sext, 4 H, J=7.5 Hz, CH$_2$CH$_2$CH$_3$), 1.50 (m, 2 H, J=7.5 Hz, CH$_2$CH$_2$Si), 2.34 (m, 4 H, NCH$_2$CH$_2$), 3.20 (br s, 6 H, NCH$_2$N), 3.74 (quart, 6 H, J=7.0 Hz, OCH$_2$).

FT-IR: 2969, 2929, 2875, 2798, 1462, 1389, 1377, 1364, 1345, 1296, 1275, 1202, 1166, 1101, 1075, 1008, 976, 953, 879, 768.

Preparation of Inventive Hexahydrotriazine Compounds:

Catalyst HHT-1

In a round-bottom flask, 0.87 g of paraformaldehyde and 15 mL of n-heptane were mixed under a nitrogen atmosphere and cooled by means of an ice bath. Subsequently, a mixture of 11.52 g of guanidine G2 and 1.87 g of n-hexylamine was stirred in in portions and then the mixture was heated to 40° C. while stirring for 3 hours. The reaction mixture was then cooled down to room temperature, washed with 10 mL of water, dried with magnesium sulfate and filtered. Thereafter, the reaction mixture was freed of the volatile constituents under reduced pressure. This gave 11.68 g of an odorless, yellow, very mobile oil.

$^{13}$C NMR (CDCl$_3$): 0.13 (CH$_3$), 13.02 (CH$_3$), 14.86 (CH$_2$), 21.56 (CH$_2$), 23.31-24.75 (CH$_2$), 24.74 (CH$_2$), 25.82 (CH$_2$), 26.19 (CH$_2$), 26.59 (CH$_2$), 29.42 (CH$_2$), 30.76 (CH$_2$), 33.23 (CH$_2$), 51.88 (CH$_2$), 62.37 (CH$_2$), 73.71 (NCH$_2$N), 151.87 (C).

FT-IR: 2959, 2927, 2854, 1645, 1450, 1410, 1363, 1257, 1066, 1015, 862, 791, 699.

Catalyst HHT-2

In a round-bottom flask, 2.03 g of guanidine G1, 4.57 g of guanidine G2 and 10 mL of n-heptane were mixed under a nitrogen atmosphere and cooled by means of an ice bath. Then 1.03 g of aqueous formaldehyde solution (37% by weight) were stirred in in portions and the mixture was subsequently stirred at room temperature for 4 hours. The reaction mixture was then washed with 10 mL of water, dried with magnesium sulfate and filtered. Thereafter, the reaction mixture was freed of the volatile constituents under reduced pressure. This gave 3.64 g of an oderless colorless oil having a viscosity at 25° C. of 2.5 Pa s.

$^{13}$C NMR (CDCl$_3$): 0.13 (CH$_3$), 14.09 (CH$_3$) 20.55 (CH$_2$), 21.43 (CH$_2$), 21.92 (CH$_2$), 23.9-24.8 (CH$_2$), 32.94 (CH$_2$), 33.31 (CH$_2$), 40.78 (CH$_2$), 46.68 (CH$_2$), 47.16 (CH$_2$), 47.78 (CH$_2$), 48.54 (CH$_2$), 49.39 (CH$_2$), 50.34 (CH), 73.12 (NCH$_2$N), 78.45 (CH$_2$), 151.7 (C).

FT-IR: 2958, 2925, 2852, 1634, 1504, 1449, 1410, 1361, 1346, 1257, 1015, 791, 701.

Catalyst HHT-3

In a round-bottom flask, 3.27 g of guanidine G1, 2.62 g of guanidine G4 and 10 mL of n-heptane were mixed under a nitrogen atmosphere and cooled by means of an ice bath. Then 1.53 g of aqueous formaldehyde solution (37% by weight) were stirred in in portions and the mixture was subsequently stirred at room temperature for 2 hours. The reaction mixture was then washed with 10 mL of water, dried with magnesium sulfate and filtered. Thereafter, the reaction mixture was freed of the volatile constituents under reduced pressure. This gave 4.95 g of an odorless yellow viscous oil having a viscosity at 25° C. of 159.8 Pa s.

$^{13}$C NMR (CDCl$_3$): 13.9 (CH$_3$), 17.23 (CH$_3$), 20.55 (CH$_2$), 22.58 (CH$_2$), 21.92 (CH$_2$), 24.6-26.0 (CH$_2$), 31.84 (CH$_2$), 33.67-34.0 (CH$_2$), 35.39 (CH$_2$), 41.59 (CH$_2$), 47.64 (CH$_2$), 49.56 (CH$_2$), 51.38 (CH), 64.26 (CH$_2$), 74.89-75.15 (NCH$_2$N), 79.42 (CH$_2$), 151.7 (C).

FT-IR: 3355, 2922, 2850, 1633, 1498, 1447, 1363, 1336, 1256, 1146, 1107, 1052, 978, 888, 872, 800, 718.

Catalyst HHT-4

In a round-bottom flask, 3.04 g of guanidine G1, 3.41 g of guanidine G5 and 10 mL of toluene were mixed under a nitrogen atmosphere. Then 0.50 g of paraformaldehyde was stirred in in portions at room temperature and the mixture was then stirred at 70° C. for 1 hour. Subsequently, the reaction mixture was cooled down to room temperature, 10 mL of toluene were added, and the mixture was dried with magnesium sulfate and filtered. Thereafter, the reaction mixture was freed of the volatile constituents under reduced pressure. This gave 6.54 g of an odorless yellow oil having a viscosity at 25° C. of 27.8 Pa s.

$^{13}$C NMR (CDCl$_3$): 17.08-17.59 (CH$_3$), 19.61-19.65 (CH$_3$), 22.30 (CH$_3$), 24.6-26.0 (CH$_2$), 33.6-34.0 (CH$_2$), 35.39 (CH$_2$), 42.45 (CH$_2$), 47.64 (CH$_2$), 49.56 (CH$_2$), 51.38 (CH), 64.26 (CH$_2$), 72.91 and 73.37 (NCH$_2$N), 74.91-75.50 (CH), 76.1-76.37 (CH$_2$), 155.83 (C).

FT-IR: 3295, 2923, 2850, 1634, 1497, 1448, 1371, 1341, 1255, 1237, 1100, 1020, 977, 926, 906, 888, 845, 807, 730, 695.

Catalyst HHT-5

In a round-bottom flask, 1.13 g of amidine A1 and 6.02 g of Wacker® Aminöl 446011-20 VP were mixed under a nitrogen atmosphere and cooled by means of an ice bath. Then 0.36 g of paraformaldehyde was stirred in in portions and the mixture was subsequently stirred at room temperature for 1 hour. Then 15 mL of tetrahydrofuran were added, and the mixture was washed with 10 mL of water, dried with magnesium sulfate and filtered. Thereafter, the reaction mixture was freed of the volatile constituents under reduced pressure. This gave 6.88 g of an odorless white oil having a viscosity at 25° C. of 2.8 Pa s.

$^{13}$C NMR (CDCl$_3$): 0.13 (CH$_3$), 14.69 (CH$_2$), 17.24 (CH$_3$), 21.0 (CH$_2$), 21.38 (CH$_3$), 23.29 (CH$_2$), 24.63 (CH$_2$), 28.07 (CH$_2$), 29.21 (CH), 29.79 (CH), 43.5 (CH$_2$), 44.93 (CH$_2$), 52.0 (CH$_2$), 59.26 (CH$_2$), 65.44 (CH$_2$), 66.95 (CH$_2$), 68.49 (NCH$_2$N), 152.8 (C).

FT-IR: 2962, 2906, 1445, 1412, 1258, 1011, 863, 795, 700.

Catalyst HHT-6

In a round-bottom flask, 4.22 g of amidine A1, 1.53 g of Jeffamine® D-230 and 12 mL of methanol were mixed under a nitrogen atmosphere and cooled by means of an ice bath. Then 1.11 g of paraformaldehyde was stirred in in portions and the mixture was subsequently stirred at room temperature for 1 hour. 10 mL of ethyl acetate were then added to the reaction mixture, which was dried with magnesium sulfate and filtered. Thereafter, the reaction mixture was freed of the volatile constituents under reduced pressure. This gave 6.74 g of an odorless colorless oil having a viscosity at 25° C. of 34.7 Pa s.

$^{13}$C NMR (CDCl$_3$): 17.23 (CH$_3$), 18.37 (CH$_3$), 21.61-21.7 (CH$_2$), 21.84-22.02 (CH$_3$), 28.85 (CH$_2$), 29.04 (CH$_2$), 43.63-43.91 (CH$_2$), 45.76 (CH$_2$), 49.05-49.92 (CH), 50.77 (CH$_2$), 52.95 (CH$_2$), 53.38 (CH), 54.38 (CH), 55.41 (CH), 60.13 (CH$_2$), 74.94 (NCH$_2$N), 153.96 (C).

FT-IR: 3233, 2926, 2850, 1612, 1425, 1374, 1318, 1292, 1208, 1100, 1085, 1015, 943, 737, 654.

Catalyst HHT-7

An initial charge of 5.28 g of amidine A1 in a round-bottom flask under a nitrogen atmosphere was cooled by means of an ice bath. Then 1.02 g of paraformaldehyde was stirred in in portions and the mixture was subsequently heated to 40° C. while stirring for 1 hour. The reaction mixture was then cooled down to room temperature, 15 mL of ethyl acetate were added, and the mixture was dried with magnesium sulfate and filtered. Thereafter, the reaction mixture was freed of the volatile constituents under reduced pressure. This gave 4.69 g of an odorless yellow oil having a viscosity at 25° C. of 52.1 Pa s.

$^{13}$C NMR (CDCl$_3$): 0.13 (CH$_3$), 12.96 (CH$_3$), 14.69 (CH$_2$), 20.41 (CH$_2$), 21.56 (CH$_2$), 23.31 (CH$_2$), 25.82 (CH$_2$), 26.19 (CH$_2$), 26.59 (CH$_2$), 29.41 (CH$_2$), 30.57 (CH$_2$), 30.76 (CH$_2$), 44.90 (CH$_2$), 48.19 (CH$_2$), 48.64 (CH), 51.96 (CH$_2$), 55.20 (CH$_2$), 62.38 (CH$_2$), 65.44 (CH$_2$), 75.0 (NCH$_2$N), 151.81 (C).

FT-IR: 3260, 2927, 2849, 1643, 1609, 1466, 1426, 1376, 1317, 1292, 1210, 1086, 1031, 945, 890, 813, 737, 693.

Catalyst HHT-8

In a round-bottom flask, 3.69 g of amidine A1, 1.06 g of 3-dimethylamino-1-propylamine and 15 mL of methylene chloride were mixed under a nitrogen atmosphere. Then 0.97 g of paraformaldehyde was stirred in in portions at room temperature and the mixture was then stirred at 40° C. for 1 hour. Subsequently, the reaction mixture was cooled down to room temperature, 10 mL of methylene chloride were added, and the mixture was dried with magnesium sulfate and filtered. Thereafter, the reaction mixture was freed of the volatile constituents under reduced pressure. This gave 4.13 g of an odorless yellow oil having a viscosity at 25° C. of 41.7 Pa s.

$^{13}$C NMR (CDCl$_3$): 14.1 (CH$_2$), 21.91 and 22.4 (CH$_3$), 25.9-26.43 (CH$_2$), 28.56 (CH$_2$), 29.13 (CH$_2$), 35.42 (CH$_2$), 44.15 (CH$_2$), 45.6 (CH$_3$), 49.08-49.48 (CH$_2$), 50.81 (CH$_2$), 57.77-57.85 (CH$_2$), 60.23 (CH$_2$), 61.28 (CH$_2$), 74.42-74.67 (NCH$_2$N), 153.29 and 153.87 (C).

FT-IR: 3255, 2926, 2850, 2812, 2762, 1612, 1551, 1457, 1424, 1374, 1317, 1292, 1206, 1098, 1084, 1061, 1040, 1012, 967, 941, 891, 835, 796, 746, 653.

Catalyst HHT-9

In a round-bottom flask, 1.00 g of amidine A1 and 3.17 g of guanidine G3 were mixed under a nitrogen atmosphere and cooled by means of an ice bath. Then 0.29 g of paraformaldehyde was stirred in in portions and the mixture was subsequently heated to 40° C. while stirring for 1 hour. The reaction mixture was then cooled down to room temperature, 15 mL of ethyl acetate were added, and the mixture was dried with magnesium sulfate and filtered. Thereafter, the reaction mixture was freed of the volatile constituents under reduced pressure. This gave 3.96 g of an odorless, pale yellow oil having a viscosity at 25° C. of 5.9 Pa s.

$^{13}$C NMR (CDCl$_3$): 0.15 (CH$_3$), 14.73 (CH$_2$), 20.02 (CH$_3$), 20.93 (CH$_2$), 21.50 (CH$_3$), 23.79, 24.06 and 24.71 (CH$_2$), 33.19 (CH$_2$), 43.30 (CH$_2$), 44.95 (CH$_2$), 59.36 (CH$_2$), 73.14-73.83 (NCH$_2$N).

FT-IR: 2961, 2927, 2854, 1615, 1448, 1430, 1373, 1318, 1257, 1078, 1016, 938, 861, 792, 701.

Catalyst HHT-10

In a round-bottom flask, 2.38 g of amidine A1 and 3.23 g of guanidine G4 were mixed under a nitrogen atmosphere and cooled by means of an ice bath. Then 0.69 g of paraformaldehyde was stirred in in portions and the mixture was subsequently heated to 40° C. while stirring for 1 hour. The reaction mixture was then cooled down to room temperature, 15 mL of ethyl acetate were added, and the mixture was dried with magnesium sulfate and filtered. Thereafter, the reaction mixture was freed of the volatile constituents under reduced pressure. This gave 6.08 g of an odorless yellow oil having a viscosity at 25° C. of 308.9 Pa s.

$^{13}$C NMR (CDCl$_3$): 14.15 (CH$_3$), 17.1-17.4 (CH$_3$), 19.25 (CH$_3$), 21.0 (CH$_3$), 21.96 (CH$_2$), 22.45 (CH$_3$), 24.97 and 25.10 (CH$_2$), 25.75 (CH$_2$), 28.94 and 29.07 (CH$_2$), 33.97-34.31 (CH$_2$), 44.33 (CH$_2$), 45.85 (CH$_2$), 49.12-49.31 (CH$_2$), 49.43 (CH), 51.65 (CH), 60.3 (CH$_2$), 75.15 (NCH$_2$N).

FT-IR: 3269, 2924, 2850, 1738, 1615, 1532, 1481, 1446, 1372, 1318, 1237, 1146, 1100, 1098, 1048, 943, 861, 785, 733.

Catalyst HHT-11 @RCa928

In a round-bottom flask, 4.31 g of intermediate HZ-1 and 3.14 g of amidine A1 were mixed under a nitrogen atmosphere, the mixture was boiled at reflux at 150° C. for 4 hours and then the volatile constituents were removed under reduced pressure. This gave 5.68 g of an odorless, pale yellow, mobile oil.

$^1$H NMR (CDCl$_3$): 0.83 (t, 6 H, J=7.4 Hz, CH$_3$), 1.41 (sext, 4 H, J=7.5 Hz, CH$_2$CH$_3$), 1.60 (sept, 2 H, J=7.1 Hz, N$_{hexah}$CH$_2$CH$_2$CH$_2$N$_{amidine}$), 1.75 (m, 2 H, N$_{amidine}$CH$_2$CH$_2$CH$_2$N$_{amidine}$), 1.92 (s, 3 H, N=CCH$_3$), 2.30 (t, 4 H, J=7.7 Hz, NCH$_2$CH$_2$CH$_3$), 2.64 (t, 2 H, J=7.0 Hz, N$_{hexah}$CH$_2$CH$_2$CH$_2$), 3.10 and 3.14 (2×m, 6 H, N$_{amidine}$CH$_2$), 3.20 (br s, 6 H, NCH$_2$N).

FT-IR: 3272, 2926, 2850, 1612, 1422, 1376, 1317, 1292, 1203, 1114, 1100, 1085, 1009, 940, 878, 833, 780, 750.

Catalyst HHT-12 @RCa927

In a round-bottom flask, 3.77 g of intermediate HZ-2 and 1.56 g of amidine A1 were mixed under a nitrogen atmosphere, the mixture was boiled at reflux at 150° C. for 4 hours and then the volatile constituents were removed under reduced pressure. This gave 4.51 g of an odorless, pale yellow, mobile oil.

$^1$H NMR (CDCl$_3$): 0.56 (m, about 2.5 H, CH$_2$Si), 0.83 (t, about 4 H, J=7.4 Hz, CH$_2$CH$_2$CH$_3$), 1.15 (t, about 9 H, J=7.0 Hz, OCH$_2$CH$_3$), 1.40 (quart, about 2.5 H, J=7.5 Hz, CH$_2$CH$_2$CH$_3$), 1.50 (m, about 2.5 H, CH$_2$CH$_2$Si), 1.60 (quint, about 2 H, J=7.0 Hz, N$_{hexah}$CH$_2$CH$_2$CH$_2$N$_{amidine}$), 1.75 (m, about 2.5 H, N$_{amidine}$CH$_2$CH$_2$CH$_2$—N$_{amidine}$), 1.93 (s, about 3 H, N=CCH$_3$), 2.32 and 2.65 (m, about 5 H and m, about 1 H, N$_{hexan}$CH$_2$CH$_2$), 3.1 (br m, about 5.5 H, N$_{amidine}$CH$_2$), 3.20 (br m, about 6 H, NCH$_2$N), 3.74 (quart, about 6 H, J=7.0 Hz, OCH$_2$).

FT-IR: 3270, 2925, 2850, 1613, 1483, 1423, 1376, 1317, 1292, 1210, 1166, 1101, 1078, 1013, 943, 880, 769.

Catalyst HHT-13 @RCa961

In a round-bottom flask, 3.59 g of intermediate HZ-2 and 2.89 g of guanidine G1 were mixed under a nitrogen atmosphere, the mixture was boiled at reflux at 150° C. for 4 hours and then the volatile constituents were removed under reduced pressure. This gave 6.06 g of an odorless, pale yellow, mobile oil.

FT-IR: 3270, 2924, 2851, 1613, 1504, 1448, 1388, 1363, 1344, 1236, 1202, 1102, 1076, 1009, 955, 888, 772.

Preparation of a Noninventive Hexahydrotriazine Compound:

Catalyst R-1

An initial charge of 7.62 g of paraformaldehyde in a round-bottom flask under a nitrogen atmosphere was cooled by means of an ice bath. Then 15.0 g of isopropylamine were slowly added dropwise and stirred in and the mixture was subsequently heated to 40° C. while stirring for 1 hour. The reaction mixture was then cooled down to room temperature, 15 mL of ethyl acetate were added, and the mixture was dried with magnesium sulfate and filtered. Thereafter, the reaction mixture was freed of the volatile constituents under reduced pressure. This gave 13.14 g of a colorless oil with an aminic odor.

$^1$H NMR (CDCl$_3$): 0.99 (d, 18 H, J=6.3 Hz, CH$_3$), 2.79 (sext, 3 H, J=6.4 Hz, NCH), 3.46 (br s, 6 H, NCH$_2$N).

$^{13}$C NMR (CDCl$_3$): 10.85 (CH$_3$), 49.81 (CH), 68.46 (NCH$_2$N).

FT-IR: 2964, 2930, 2872, 2813, 1663, 1462, 1380, 1362, 1328, 1237, 1214, 1165, 1115, 1090, 1035, 1009, 988, 936, 888, 851, 785.

Overview of the Hexahydrotriazine Compounds Prepared:

TABLE 1

Reactants used and approximate molar ratios of intermediates HZ-1 and HZ-2 and catalysts HHT-1 to HHT-13 and R-1

| | | |
|---|---|---|
| HZ-1 | 3 mol n-propylamine | 3 mol formaldehyde |
| HZ-2 | 1 mol intermediate HZ-1 | 1 mol AMEO |

TABLE 1-continued

Reactants used and approximate molar ratios of intermediates HZ-1 and HZ-2 and catalysts HHT-1 to HHT-13 and R-1

| | | | |
|---|---|---|---|
| HHT-1 | 1 mol guanidine G2 | 2 mol hexylamine | 3 mol formaldehyde |
| HHT-2 | 2 mol guanidine G1 | 1 mol guanidine G2 | 3 mol formaldehyde |
| HHT-3 | 2 mol guanidine G1 | 1 mol guanidine G4 | 3 mol formaldehyde |
| HHT-4 | 2 mol guanidine G1 | 1 mol guanidine G5 | 3 mol formaldehyde |
| HHT-5 | 2 mol amidine A1 | 1 mol Wacker ® Aminol 446011-20 VP | 3 mol formaldehyde |
| HHT-6 | 4 mol amidine A1 | 1 mol Jeffamine ® D-230 | 6 mol formaldehyde |
| HHT-7 | 3 mol amidine A1 | | 3 mol formaldehyde |
| HHT-8 | 2 mol amidine A1 | 1 mol 3-dimethylamino-1-propylamine | 3 mol formaldehyde |
| HHT-9 | 2 mol amidine A1 | 1 mol guanidine G3 | 3 mol formaldehyde |
| HHT-10 | 2 mol amidine A1 | 1 mol guanidine G4 | 3 mol formaldehyde |
| HHT-11 @RCa928 | 1 mol intermediate HZ-1 | | 1 mol amidine A1 |
| HHT-12 @RCa927 | 1 mol intermediate HZ-2 | | 1 mol amidine A1 |
| HHT-13 @RCa961 | 1 mol intermediate HZ-2 | | 1 mol guanidine G1 |
| R-1 | 3 mol isopropylamine | | 3 mol formaldehyde |

TABLE 2

Idealized structure[1] of intermediates HZ-1 and HZ-2 and catalysts HHT-1 to HHT-13 and R-1

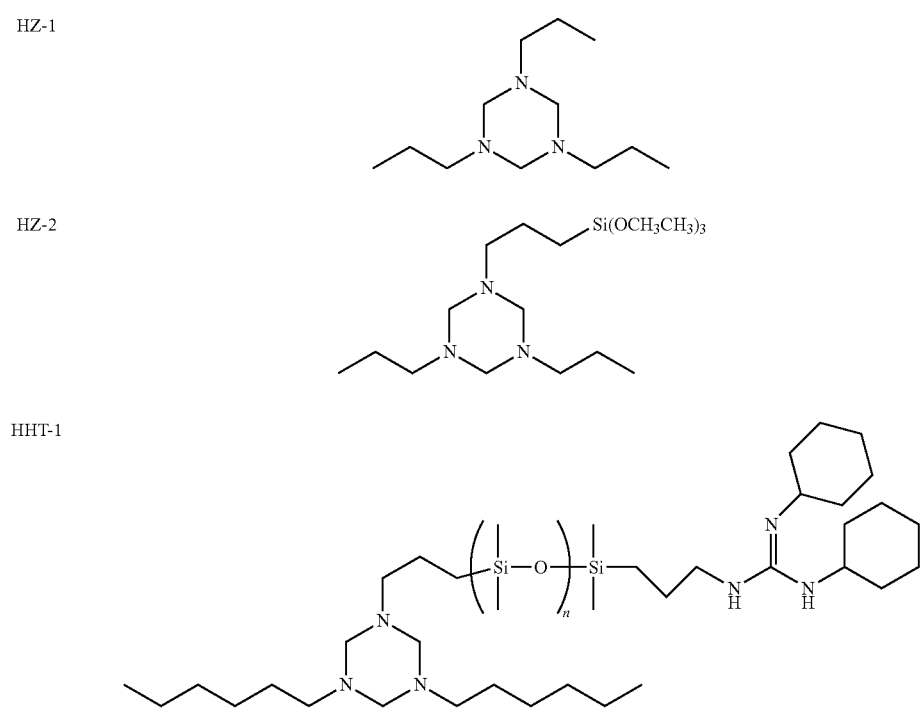

TABLE 2-continued
Idealized structure[1] of intermediates HZ-1 and HZ-2 and catalysts HHT-1 to HHT-13 and R-1
HHT-2
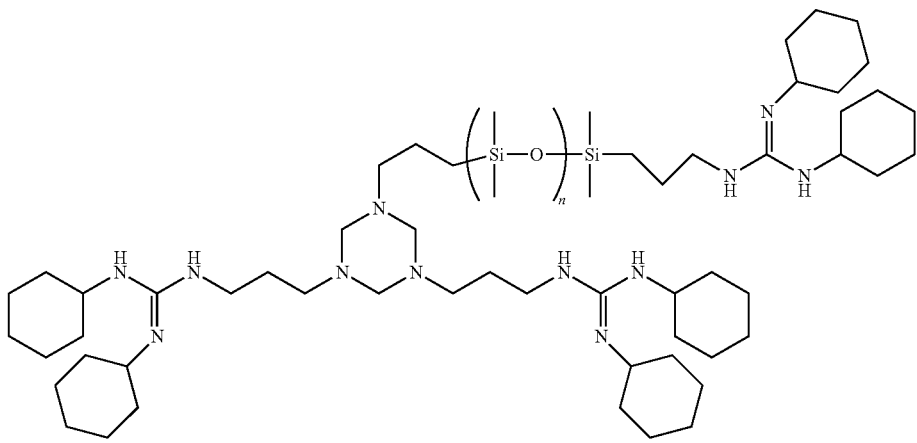
HHT-3
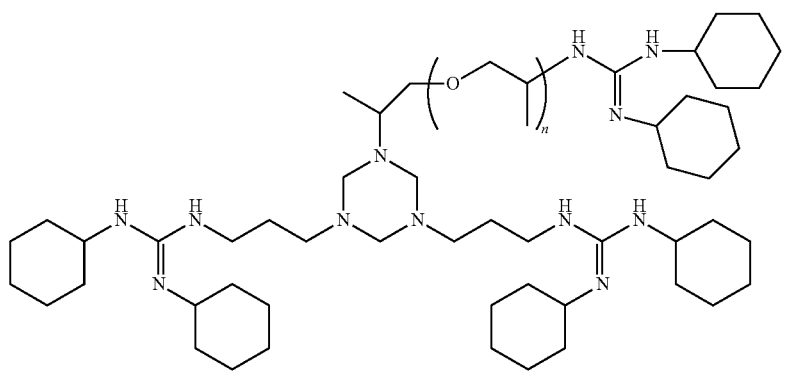
HHT-4
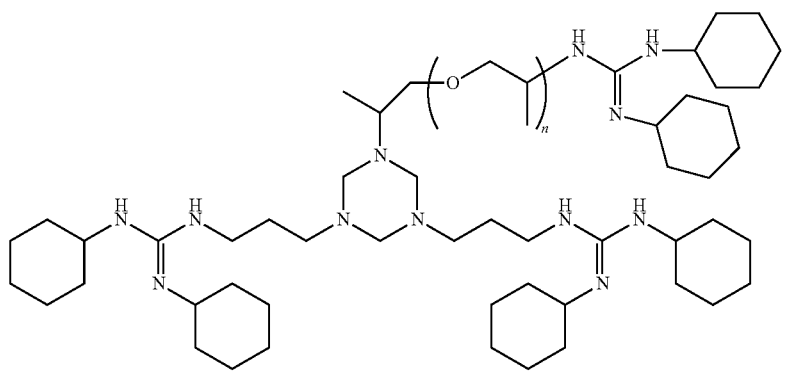
HHT-5
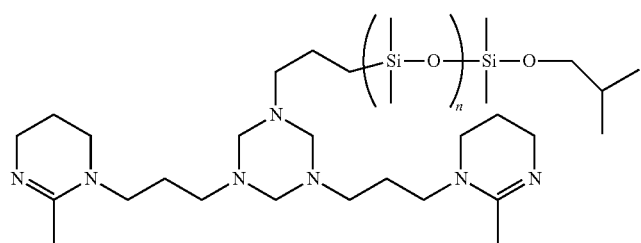

TABLE 2-continued
Idealized structure[1] of intermediates HZ-1 and HZ-2 and catalysts
HHT-1 to HHT-13 and R-1
HHT-6
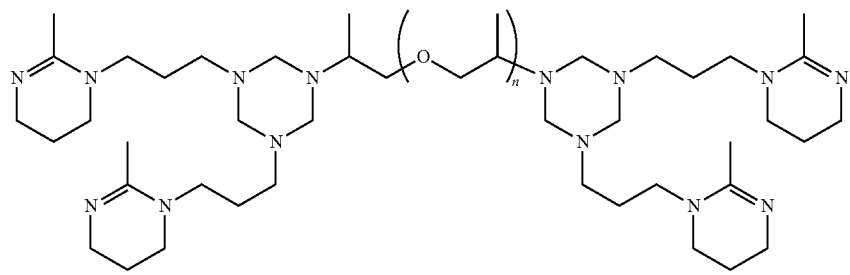
HHT-7
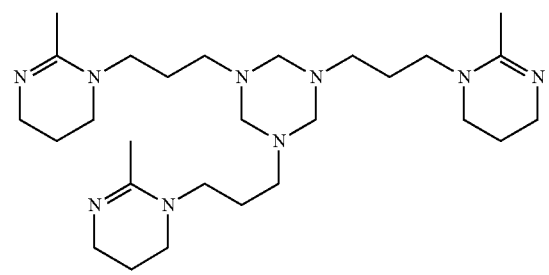 [SMILES: CC1=NCCCN1CCCN1CN(CCCN2CCCN=C2C)CN(CCCN2CCCN=C2C)C1]
HHT-8
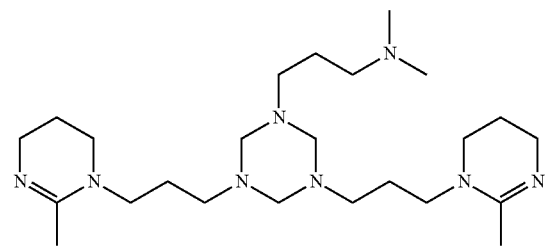 [SMILES: CC1=NCCCN1CCCN1CN(CCCN(C)C)CN(CCCN2CCCN=C2C)C1]
HHT-9
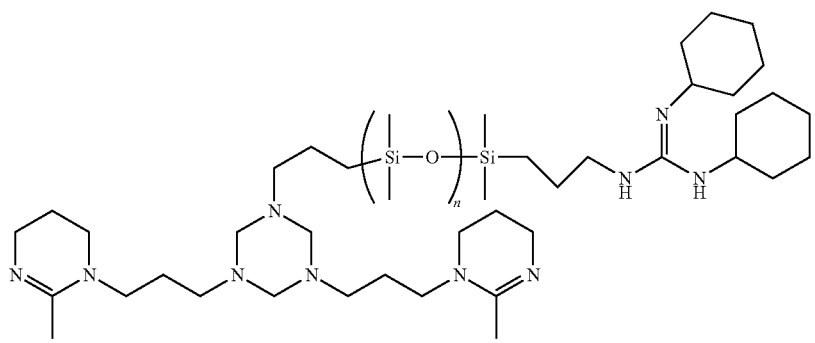
HHT-10
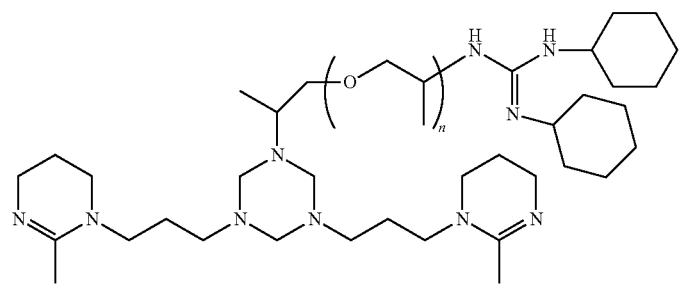

TABLE 2-continued

Idealized structure[1] of intermediates HZ-1 and HZ-2 and catalysts
HHT-1 to HHT-13 and R-1

HHT-11

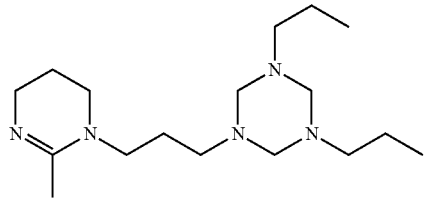 [SMILES: CCCN1CN(CCC)CN(CCCN2CCCN=C2C)C1]

HHT-12

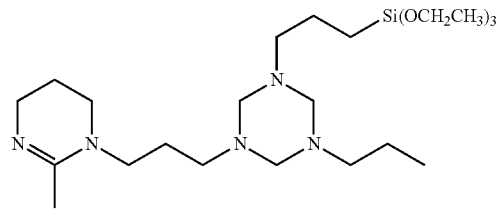

HHT-13

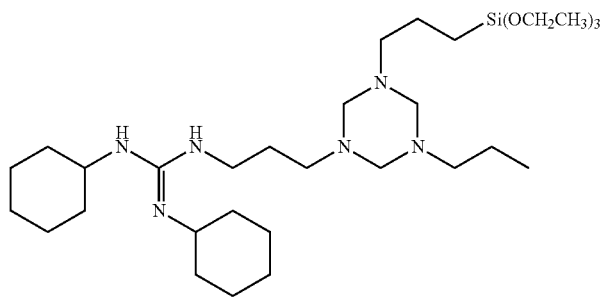

R-1

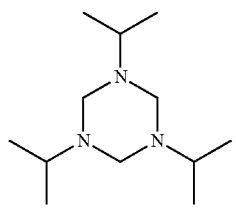

[1] The "idealized structure" refers to a structure that reflects the stoichiometric ratios. Of course, the reaction product, as well as this compound, contains proportions of further reaction products, especially those in which the substituents on the hexahydrotriazine unit are distributed differently.

Preparation of Polyethers Having Silane Groups:
Polymer STP-1:

With exclusion of moisture, 1000 g of Acclaim® 12200 polyol (polyoxypropylenediol having a low level of unsaturation, from Covestro; OH number 11.0 mg KOH/g), 43.6 g of isophorone diisocyanate (IPDI; Vestanat® IPDI, from Evonik), 126.4 g of diisononyl cyclohexane-1,2-dicarboxylate (DINCH) and 0.1 g of bismuth tris(neodecanoate) (10% by weight in DINCH) were heated up to 90° C. while stirring constantly and left at this temperature until the content of free isocyanate groups determined by titrimetry had reached a stable value of 0.63% by weight. Subsequently, 63.0 g of diethyl N-(3-trimethoxysilylpropyl)aminosuccinate (adduct of 3-aminopropyltrimethoxysilane and diethyl maleate; produced as per U.S. Pat. No. 5,364,955) were mixed in and the mixture was stirred at 90° C. until it was no longer possible to detect any free isocyanate by FT-IR spectroscopy. The polyether having trimethoxysilane groups thus obtained, having a silane equivalent weight of about 6880 g/eq (calculated from the amounts used), was cooled down to room temperature and stored with exclusion of moisture.

Commercial Catalysts Used:
Cat.41 Reaction product of tetraethyl silicate with bis (acetyloxy)dibutylstannane, tin content about 23.8% by weight (Catalyst 41, from Wacker)
DBU 1,8-diazabicyclo[5.4.0]undec-7-ene (Lupragen® N 700, from BASF)
TMHHT 1,3,5-trimethylhexahydro-1,3,5-triazine (Sigma-Aldrich)
Compositions Based on Polymers Having Silane Groups:
Comparative examples in tables 3 to 6 are indicated by "(ref.)".
Compositions Z1 to Z11:

In a round-bottom flask, 71.1 g of an OH-terminated linear polydimethylsiloxane having a viscosity of about 50,000 mPas (Wacker® Silicone Rubber Polymer FD 50, from Wacker) were blended at room temperature with 2.6 g of vinyltris(methylethylketoximo)silane and stirred under reduced pressure for 15 minutes. 26.3 g of trimethylsilyl-terminated polydimethylsiloxane (Wacker® AK 100 silicone oil, from Wacker) were stirred into the polydimethylsiloxane having vinylbis(methylethylketoximo)silyl end groups that was obtained in this way. This mixture was blended with various catalysts according to table 3 below and the mixture was tested for viscosity at 25° C. and skin time (ST) under standard climatic conditions, before and after storage. The skin time serves as a measure of the activity of the catalyst in relation to the crosslinking reaction of the silane groups, i.e. of the crosslinking rate; the change in viscosity and the skin time after storage are a measure of storage stability of the composition. In addition, the mixture applied, after 24 hours under standard climatic conditions, was tested as to whether the surface was dry as desired or whether a greasy film had formed, which is a sign of the exudation of the catalyst owing to poor compatibility with the cured polymer, and/or whether the surface was tacky, which is a sign of incomplete curing. In addition, the mixture was used to produce a film of thickness 2 mm, which was cured under standard climatic conditions for 7 days and tested for mechanical properties.

The results are shown in tables 3 and 4.

TABLE 3

| Composition | Catalyst | Amount | Concentration[1] | Viscosity [Pa · s] fresh | Viscosity [Pa · s] stored[2] | ST fresh | ST stored[2] |
|---|---|---|---|---|---|---|---|
| Z1 | HHT-1 | 0.57 g | 0.5 | 11.8 | 12.3 | 18' | 15' |
| Z2 | HHT-4 | 0.15 g | 0.5 | 12.2 | 12.7 | 16' | 17' |
| Z3 | HHT-6 | 0.09 g | 0.5 | 11.9 | 12.1 | 20' | 18' |
| Z4 | HHT-7 | 0.06 g | 0.5 | 11.6 | 12.1 | 65' | 70' |
| Z5 | HHT-8 | 0.09 g | 0.5 | 12.0 | 12.0 | 35' | 30' |
| Z6 | HHT-9 | 0.18 g | 0.5 | 13.6 | 14.5 | 20' | 14' |
| Z7 | HHT-10 | 0.10 g | 0.5 | 13.0 | 13.7 | 25' | 16' |
| Z8 (ref.) | R-1 | 0.08 g | — | 12.6 | 12.8 | 2 h 25' | 1 h 56' |
| Z9 (ref.) | TMHHT | 0.05 g | — | 11.9 | 18.4 | 2 h 30' | 1 h 58' |
| Z10 (ref.) | — | — | — | 11.9 | 12.2 | 2 h 36' | 2 h 10' |
| Z11 (ref.) | Cat.41 | 0.33 g | 1.1 | 11.7 | 48.1 | 27' | 32' |

[1]mmol of amidine or guanidine groups or metal atoms per 100 g of ketoximato polydimethylsiloxane polymer.
[2]for 7 days at 70° C. in a closed container.

TABLE 4

| Composition | Surface after 24 h | Tensile strength | Elongation at break | Modulus of elasticity 0-25% elongation |
|---|---|---|---|---|
| Z1 | dry | n.d. | n.d. | n.d. |
| Z2 | dry | 0.22 MPa | 183% | 0.18 MPa |
| Z3 | dry | 0.17 MPa | 126% | 0.18 MPa |
| Z4 | dry | 0.18 MPa | 103% | 0.18 MPa |
| Z5 | dry | 0.14 MPa | 81% | 0.17 MPa |
| Z6 | dry | 0.23 MPa | 234% | 0.18 MPa |
| Z7 | dry | 0.22 MPa | 129% | 0.20 MPa |
| Z8 (ref.) | dry | n.d. | n.d. | n.d. |
| Z9 (ref.) | dry | n.d. | n.d. | n.d. |
| Z10 (ref.) | dry | n.d. | n.d. | n.d. |
| Z11 (ref.) | dry | 0.24 MPa | 256% | 0.19 MPa |

"n.d." stands for "not determined"

Compositions Z12 to Z25:

A composition composed of 97.6 g of polymer STP-1, 2.0 g of vinyltrimethoxysilane and 0.4 g of 3-aminopropyltrimethoxysilane was blended with various catalysts in the amount specified according to table 5, and tested as described for composition Z1 for viscosity, skin time (ST), surface characteristics and mechanical properties.

The results are shown in tables 5 and 6.

TABLE 5

| Composition | Catalyst | Amount | Concentration[1] | Viscosity [Pa · s] fresh | Viscosity [Pa · s] stored[2] | ST fresh | ST stored[2] |
|---|---|---|---|---|---|---|---|
| Z12 | HHT-1 | 2.81 g | 1.9 | 28.3 | 44.0 | 17' | 11' |
| Z13 | HHT-2 | 1.16 g | 1.9 | 29.5 | 58.9 | 12' | 8' |
| Z14 | HHT-3 | 0.66 g | 1.9 | 28.4 | 61.3 | 12' | 8' |
| Z15 | HHT-5 | 1.88 g | 1.9 | 28.8 | 45.3 | 25' | 31' |
| Z16 | HHT-6 | 0.44 g | 1.9 | 51.5 | 53.5 | 25' | 22' |
| Z17 | HHT-7 | 0.31 g | 1.9 | 40.9 | 50.0 | 26' | 30' |
| Z18 | HHT-9 | 0.88 g | 1.9 | 40.8 | 52.9 | 14' | 16' |
| Z19 | HHT-10 | 0.50 g | 1.9 | 40.8 | 52.9 | 18' | 20' |
| Z20 | HHT-11 | 0.58 g | 1.9 | 17.9 | 24.2 | 24' | 26' |
| Z21 | HHT-12 | 0.89 g | 1.9 | 17.6 | 24.0 | 24' | 27' |
| Z22 | HHT-13 | 1.11 g | 1.9 | 29.9 | 52.1 | 8' | 6' |
| Z23 (ref.) | R-1 | 0.40 g | — | 28.2 | 35.4 | 77' | 90' |
| Z24 (ref.) | TMHHT | 0.24 g | — | 29.5 | 34.2 | 80' | 90' |
| Z25 (ref.) | DBU | 0.36 g | 2.4 | 26.3 | 31.0 | 29' | 31' |

[1]mmol of amidine or guanidine groups per 100 g of polyether having silane groups.
[2]for 7 days at 70° C. in a closed container.

TABLE 6

| Composition | Surface after 24 h | Tensile strength | Elongation at break | Modulus of elasticity 0-5% | Modulus of elasticity 0-50% |
|---|---|---|---|---|---|
| Z12 | dry | 0.77 MPa | 126% | 1.22 MPa | 0.84 MPa |
| Z13 | dry | 0.75 MPa | 110% | 1.23 MPa | 0.85 MPa |
| Z14 | dry | 0.75 MPa | 104% | 1.25 MPa | 0.88 MPa |
| Z15 | slightly greasy | 0.68 MPa | 97% | 1.09 MPa | 0.82 MPa |
| Z16 | dry | 0.67 MPa | 96% | 1.20 MPa | 0.82 MPa |
| Z17 | dry | 0.75 MPa | 108% | 1.15 MPa | 0.87 MPa |
| Z18 | dry | 0.73 MPa | 100% | 1.11 MPa | 0.87 MPa |
| Z19 | dry | 0.72 MPa | 91% | 1.18 MPa | 0.86 MPa |
| Z20 | dry | 0.80 MPa | 102% | 1.30 MPa | 0.87 MPa |
| Z21 | dry | 0.73 MPa | 88% | 1.28 MPa | 0.87 MPa |
| Z22 | dry | 0.64 MPa | 76% | 1.37 MPa | 0.84 MPa |
| Z23 (ref.) | dry | 0.67 MPa | 94% | 1.30 MPa | 0.86 MPa |
| Z24 (ref.) | dry | 0.66 MPa | 88% | 1.21 MPa | 0.88 MPa |
| Z25 (ref.) | greasy | 0.70 MPa | 95% | 0.98 MPa | 0.79 MPa |

Two-Component Polyurethane Compositions:

Comparative examples in table 7 are indicated by "(ref.)".

Compositions Z26 to Z29

A first component was prepared by mixing 20.00 g of Poly bd® R-45HTLO with the amount of catalyst specified in table 7.

The second component used was 2.65 g of Desmodur® CD.

The two components were mixed and the skin time was determined immediately.

The results are shown in table 7.

| Composition | Catalyst | Amount | Concentration[1] | ST |
|---|---|---|---|---|
| Z26 | HHT-8 | 0.08 g | 1.8 | 26' |
| Z27 (ref.) | DBU | 0.03 g | 1.2 | 25' |
| Z28 (ref.) | TMHHT | 0.03 g | — | 62' |
| Z29 (ref.) | — | — | — | 65' |

[1]mmol of amidine or guanidine groups per 100 g of polyol.

The invention claimed is:

1. A compound containing at least one hexahydrotriazine unit of the formula (I)

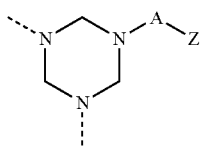

where
A is a divalent hydrocarbyl radical optionally containing heteroatoms, and
Z is an amidine or guanidine group bonded via a nitrogen atom,
where the hexahydrotriazine ring and the Z group are separated from one another by a chain of at least two carbon atoms.

2. A compound as claimed in claim 1, wherein A is a divalent hydrocarbyl radical which has 2 to 50 carbon atoms and optionally contains heteroatoms in the form of ether oxygen or secondary or tertiary amine nitrogen or siloxane units.

3. A compound as claimed in claim 1, wherein Z is

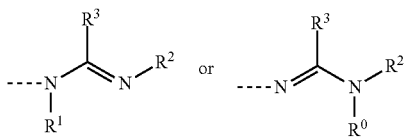

where
$R^0$ is a hydrogen radical or an alkyl or cycloalkyl or aralkyl radical having 1 to 8 carbon atoms,
$R^1$ is a hydrogen radical or an alkyl or cycloalkyl or aralkyl radical having 1 to 8 carbon atoms or together with $R^2$ is $R^6$,
$R^2$ is a hydrogen radical or an alkyl, cycloalkyl or aralkyl radical which has 1 to 18 carbon atoms and optionally contains ether oxygen or tertiary amine nitrogen, or together with $R^1$ is $R^6$,
$R^3$ is —$NR^4R^5$ or a hydrogen radical or an alkyl or cycloalkyl or aralkyl radical having 1 to 12 carbon atoms,
where
$R^4$ and $R^5$ are each independently a hydrogen radical or an alkyl, cycloalkyl or aralkyl radical which has 1 to 18 carbon atoms and optionally contains ether oxygen or tertiary amine nitrogen,
$R^6$ is an optionally substituted 1,2-ethylene, 1,3-propylene or 1,4-butylene radical having 2 to 12 carbon atoms,
$R^2$ and $R^0$ together may also be an alkylene radical which has 3 to 6 carbon atoms and optionally contains ether oxygen or tertiary amine nitrogen,
$R^2$ and $R^3$ together may also be an alkylene radical having 3 to 6 carbon atoms,
$R^4$ and $R^5$ together may also be an alkylene radical which has 4 to 7 carbon atoms and optionally contains ether oxygen or tertiary amine nitrogen, and
$R^2$ and $R^5$ together may also be an alkylene radical having 2 to 12 carbon atoms.

4. A compound as claimed in claim 3, wherein $R^3$ is a hydrogen radical or an alkyl radical having 1 to 4 carbon atoms, and $R^1$ and $R^2$ together are $R^6$.

5. A compound as claimed in claim 3, wherein $R^3$ is —$NR^4R^5$, $R^1$, $R^0$ and $R^4$ are each a hydrogen radical, and $R^2$ and $R^5$ are each independently an alkyl, cycloalkyl or aralkyl radical which has 1 to 12 carbon atoms and optionally contains an ether oxygen or tertiary amine nitrogen.

6. A compound as claimed in claim 1, wherein it is selected from compounds of the formula (II) and compounds of the formula (III)

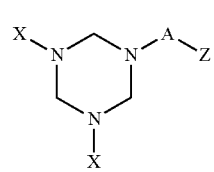

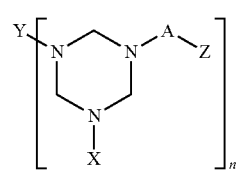

where
X is -A-Z or a monovalent hydrocarbyl radical which has 1 to 30 carbon atoms and optionally contains heteroatoms,
Y is an n-valent hydrocarbyl radical which has 2 to 30 carbon atoms and optionally contains heteroatoms, and
n is 2 or 3,
where, in the case of compounds of the formula (III), the hexahydrotriazine rings are each separated from one another by a chain of at least two carbon atoms.

7. A compound as claimed in claim 6, wherein X is a radical selected from -A-Z, methyl, ethyl, propyl, isopropyl, butyl, isobutyl, sec-butyl, tert-butyl, hexyl, octyl, 2-ethylhexyl, cyclohexyl, benzyl, methoxyethyl, methoxyethoxyethyl, trimethoxysilylpropyl, triethoxysilylpropyl and ω-alkoxypoly(dimethylsiloxane)prop-3-yl having an average molecular weight in the range from about 350 to 2,000 g/mol.

8. A process for preparing the compound as claimed in claim 1, wherein at least one amine of the formula $H_2N$-A-Z and at least one further primary amine are reacted with formaldehyde or a formaldehyde-releasing compound with removal of water.

9. A method comprising applying a compound as claimed in claim 1 as catalyst for the crosslinking of a functional compound.

10. The method as claimed in claim 9, wherein the functional compound is a polyisocyanate or a polyurethane polymer having isocyanate groups or a polymer having silane groups.

11. The method as claimed in claim 10, wherein the functional compound is a polymer having silane groups selected from the group consisting of polyorganosiloxanes having terminal silane groups and organic polymers having silane groups.

12. A curable composition comprising at least one compound as claimed in claim 1 as catalyst.

13. The curable composition as claimed in claim 12, wherein it contains isocyanate groups and/or silane groups.

14. The curable composition as claimed in claim 12, wherein it is an adhesive or a sealant or a coating.

15. The curable composition as claimed in claim 12, wherein it comprises at least one further constituent selected from the group consisting of fillers, plasticizers, rheology additives, desiccants, adhesion promoters and crosslinkers.

* * * * *

UNITED STATES PATENT AND TRADEMARK OFFICE
CERTIFICATE OF CORRECTION

| | | |
|---|---|---|
| PATENT NO. | : 11,097,259 B2 | Page 1 of 1 |
| APPLICATION NO. | : 16/318661 | |
| DATED | : August 24, 2021 | |
| INVENTOR(S) | : Cannas et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 303 days.

Signed and Sealed this
Thirty-first Day of January, 2023

Katherine Kelly Vidal
*Director of the United States Patent and Trademark Office*